(12) United States Patent
Kreuter et al.

(10) Patent No.: US 11,759,492 B2
(45) Date of Patent: Sep. 19, 2023

(54) **EXTRACT FROM A PLANT OF THE GENUS *BOSWELLIA* AND RELATED PRODUCTS AND USES**

(71) Applicant: Alpinia Laudanum Institute of Phytopharmaceutical Sciences AG, Walenstadt (CH)

(72) Inventors: Matthias H. Kreuter, Walenstadt (CH); Michael Kemmler, Lörrach (DE)

(73) Assignee: Alpinia Laudanum Institute of Phytopharmaceutical Sciences AG, Walenstadt (CH)

( * ) Notice: Subject to any disclaimer, the term of this patent is extended or adjusted under 35 U.S.C. 154(b) by 1017 days.

(21) Appl. No.: 15/521,212

(22) PCT Filed: Oct. 21, 2015

(86) PCT No.: PCT/EP2015/002084
§ 371 (c)(1),
(2) Date: Apr. 21, 2017

(87) PCT Pub. No.: WO2016/062402
PCT Pub. Date: Apr. 28, 2016

(65) Prior Publication Data
US 2019/0083561 A1 Mar. 21, 2019

(30) Foreign Application Priority Data
Oct. 21, 2014 (WO) .................. PCT/EP2014/002845

(51) Int. Cl.
| | | |
|---|---|---|
| *A61K 36/324* | (2006.01) | |
| *A61K 45/06* | (2006.01) | |
| *A23L 33/105* | (2016.01) | |
| *A61K 8/9789* | (2017.01) | |
| *A23L 2/52* | (2006.01) | |
| *A61K 8/31* | (2006.01) | |
| *A61K 8/33* | (2006.01) | |
| *A61K 8/34* | (2006.01) | |
| *A61K 8/35* | (2006.01) | |
| *A61K 31/015* | (2006.01) | |
| *A61K 31/045* | (2006.01) | |
| *A61K 31/085* | (2006.01) | |
| *A61K 31/122* | (2006.01) | |
| *A61Q 19/00* | (2006.01) | |

(52) U.S. Cl.
CPC .............. *A61K 36/324* (2013.01); *A23L 2/52* (2013.01); *A23L 33/105* (2016.08); *A61K 8/31* (2013.01); *A61K 8/33* (2013.01); *A61K 8/342* (2013.01); *A61K 8/35* (2013.01); *A61K 8/9789* (2017.08); *A61K 31/015* (2013.01); *A61K 31/045* (2013.01); *A61K 31/085* (2013.01); *A61K 31/122* (2013.01); *A61K 45/06* (2013.01); *A61Q 19/00* (2013.01); *A61K 2236/33* (2013.01); *A61K 2800/10* (2013.01)

(58) Field of Classification Search
CPC ....................................................... A61K 36/00
USPC ........................................................... 424/725
See application file for complete search history.

(56) References Cited

U.S. PATENT DOCUMENTS

| | | | |
|---|---|---|---|
| 8,828,377 B2 | 9/2014 | Gokaraju et al. | |
| 2007/0231345 A1* | 10/2007 | Majeed ................. | A61K 31/28 424/195.18 |
| 2011/0159120 A1* | 6/2011 | Gokaraju ............. | A61K 36/324 424/725 |
| 2014/0301971 A1 | 10/2014 | Milbocker et al. | |

FOREIGN PATENT DOCUMENTS

| | | |
|---|---|---|
| CN | 1861122 A | 11/2006 |
| WO | 2003/020026 A1 | 3/2003 |
| WO | 2011/099029 A1 | 8/2011 |
| WO | 2011/114350 A2 | 9/2011 |
| WO | 2012/177825 A1 | 12/2012 |

OTHER PUBLICATIONS

Hamm, S. et al., A chemical investigation by headspace SPME and GC-MS of volatile and semi-volatile terpenes in various olibanum samples, Phytochemistry, 66(12): 1499-1514, May 25, 2005.
Tongnuanchan, P. et al., Essential Oils: Extraction, Bioactivities, and Their Uses for Food Preservation, Journal of Food Science, 79(7): R1231-R1249, Jul. 2, 2014.
Basar, S., Phytochemical investigations on *Boswellia* Species. Comparative studies on essential oils, pyrolisates and boswellic acids, Dissertation For the Fulfillment of the Requirements For the Degree of Dr. Rer. Nat, University of Hamburg, Hamburg, pp. 1-231, Jan. 1, 2005.
Mertens, M. et al., The volatile constituents of frankincense—a review, Flavour and Fragrance Journal, Wiley, New York, NY, 24(6): 279-300, Nov. 1, 2009.

(Continued)

*Primary Examiner* — Michael V Meller
(74) *Attorney, Agent, or Firm* — Julie K. Staple; Dinsmore & Shohl LLP

(57) ABSTRACT

The invention relates to a novel extract from the resin of a plant of the genus *Boswellia* (Burseraceae). The invention further relates to a composition comprising the novel extract, in particular a pharmaceutical composition or a cosmetic composition, or a food supplement, a food or a beverage comprising the extract. Further, the invention concerns the use of the extract and the respective compositions, in particular the use of the extract or a composition comprising the extract in the cosmetic or therapeutic field as well as in food supplements. The invention also relates to the novel extract and the respective compositions for use in the treatment and/or prevention of a disease. A method of treatment and/or prevention of a neurodegenerative disease is further provided. A process is also provided, by which the novel extract is obtained.

17 Claims, 7 Drawing Sheets

(56) References Cited

OTHER PUBLICATIONS

Sultana, A. et al., Boswellia Serrata ROXB. A Traditional Herb with Versatile Pharmacological Activity: A Review, International Journal of Pharmaceutical Sciences and Research, 4(6): 2106-2117, 2013.
Notice of Reasons for Rejection from Japanese Application No. JP 2017-521518, dated Nov. 10, 2020.
Lang, G. et al., A review on recent research results (2008-2010) on essential oils as antimicrobials and antifungals. A review, Flavour and Fragrance Journal, 27(1): 13-39, Aug. 16, 2011.
EMEA/HMPC/137212/2005, Committee on Herbal Medicinal products, Nov. 23, 2005, http://www.ema.europa.eu/docttp://www.ema.europa.eu/docs/en_GB/document_library/Scientific_guideline/2010/04/WC500089960.pdf.

\* cited by examiner

A.

B.

C.

D.

C.

D.

EXTRACT FROM A PLANT OF THE GENUS BOSWELLIA AND RELATED PRODUCTS AND USES

CROSS REFERENCE TO RELATED APPLICATIONS

This application is a US National phase application of PCT/EP2015/002084, filed Oct. 21, 2015 which claims priority to PCT/EP2014/002845, filed Oct. 21, 2014.

TECHNICAL FIELD OF THE INVENTION

The invention relates to a novel extract from a resin of a plant of the genus *Boswellia* (Burseraceae). The invention further relates to a composition comprising the novel extract, in particular a pharmaceutical composition or a cosmetic composition, or a food supplement, a food or a beverage comprising the extract. Further, the invention concerns the use of the extract and the respective compositions, in particular the use of the extract or a composition comprising the extract in the cosmetic or therapeutic field as well as in food supplements. The invention also relates to the novel extract and the respective compositions for use in the treatment and/or prevention of a disease. A method of treatment and/or prevention of a neurodegenerative disease is further provided. A process is also provided, by which the novel extract is obtained.

TECHNICAL BACKGROUND

The pharmaceutical tradition of the gum resin derived from the bark of trees of the *Boswellia* spp. (Burseracea) dates back three thousand years and there is a stringent usage in both folkloric as well as modern phytomedicine up to now. This is also accounted for by the inclusion of the drug in pharmacopeial monographs (Ergänzungsband zum Deutschen Arzneibuch 4, 1916; Pharmacopée francaise 1949; Ergänzungsband zum Deutschen Arzneibuch 6, 1953, European Pharmacopeia Ph. Eur. 8, 2014, European Scientific Cooperative on Phytotherapy (ESCOP), second edition, Supplement 2009 (Olibanum Indicum ESCOP Monographs).

Olibanum indicum, Indian Frankincense, consists of the air-dried gum-resin exudates obtained by incision in the stem or branches from the Indian Olibanum, Salai or Saphal tree (Kreck and Saller, 1998), *Boswellia serrata* ROXB (Burseracea). The gum resin of *Boswellia serrata*, known in the vernacular as "Sallai guggal", has been used in the Ayurvedic system of medicine for the management of rheumatism, respiratory diseases and liver disorders. Indian Frankincense contains essential oils, resin and slime (for an overview see Blaschek, W. et al., Drogen A-K, Folgeband 2 in: Hagers Handbuch der Pharmazeutischen Praxis, 5., vollständig neu bearbeitete Auflage, 1998, Berlin, Heidelberg, N.Y.).

In accordance with that concept established by traditional medicine, *Boswellia* extract as well as individual components of the extract have been shown in vitro and in vivo to have anti-inflammatory and immunomodulatory activities. For instance, EP 552657 describes the use of boswellic acids and their salts for the treatment of inflammations caused by increased leucocyte generation.

The main characteristic constituents in *Boswellia* extracts, which account for around 20-30% (w/w) of Olibanum's lipophilic extractives are pentacyclic triterpenic acids (boswellic acids and derivatives thereof, such as 11-keto-ß-boswellic-acid (KBA), acetyl-11-keto-ß-boswellic-acid (AKBA), ß-boswellic-acid, acetyl-ß-boswellic-acid, α-boswellic-acid and acetyl-α-boswellic-acid) and tetracyclic triterpenic acids (tirucallic acids).

Based on numerous studies, boswellic acids are currently considered as one of the active principles of *Boswellia* resins (see, for example, the studies cited in the ESCOP monograph 'Olibanum indicum'). 11-keto-ß-boswellic-acid (KBA) and acetyl-11-keto-ß-boswellic-acid (AKBA) (Safayhi et al., Boswellic acids: novel, specific, nonredox inhibitors of 5-lipoxygenase. J. Pharmacol. Exp. Ther. 1143-1146, 1992); Sailer, E. R. et al., Structure-activity relationships of the nonredox-type non-competitive leukotriene biosynthesis inhibitor acetyl-11-keto-β-boswellic acid. Phytomedicine 4, 73-74, 1996; Schneider, G. et al., 1999, Arzneidrogen, 4. Aufl., Spektrum Akademischer Verlag, Heidelberg) are described as marker substances in the Ph. Eur. monograph of Olibanum indicum. (Olibanum Indicum; Paul, M., Chemotaxonomic Investigations on Resins of the Frankincense Species *Boswellia papyrifera*, *Boswellia serrata* and *Boswellia sacra*, respectively, *Boswellia carterii*. Diss rer. nat. Universität Saarland 2012; Tausch, L. et al, Identification of human cathepsin G as a functional target of boswellic acids from the anti-inflammatory remedy frankincense. J Immunol, 183, 3433-3442, 2009; Stürner, K. H. et al., Boswellic acids reduce Th17 differentiation via blockade of IL-1β-mediated IRAK1 signaling, Eur J Immunol. 2014 April; 44(4):1200-12).

Furthermore, some *Boswellia* extracts comprise characteristic compounds of the cembrene class of diterpenes, namely serratol and incensole or its acetate (Safayhi, H. et al., Pharmakologische Aspekte von Weihrauch and Boswelliasäuren, PZ 142 (39), 11-20, 1997). Incensolacetate was also found to be pharmacologically active and to cause anti-inflammatory effects and immune modulation (Moussaieff, A. et al., Incensole acetate, a novel anti-inflammatory compound isolated from *Boswellia* resin, inhibits nuclear factor-kappa B activation. In: Molecular Pharmacology 2007 December; 72 (6):1657-1664. Epub 2007 Sep. 25; Moussaieff, A. et al., Incensole acetate, an incense component, elicits psychoactivity by activating TRPV3 channels in the brain. In: The FASEB Journal August 2008; 22(8): 3024-3034. doi: 10.1096/fj.07-101865). The international patent application WO 2008/058514 relates to the use of preparations with pentacyclic triterpenoic acids and structural derivatives thereof for inhibiting the inducible microsomal prostaglandin E2 synthase-1. In addition, the application relates to the use of pentacyclic triterpenoic acids and derivatives thereof for producing a medicament for the treatment of PGE2-mediated diseases. Furthermore it was found, that extracts from the resin, containing both triterpenic acids and cembrenes, were more effective in inhibition of mPGES-1 than it could be explained with respect to their content of boswellic acids. These results clearly indicate that cembrenes, namely the diterpenic alcohols and derivatives thereof, are contributing to the immune modulatory and anti-inflammatory profile of extracts from resins of the genus *Boswellia*. Accordingly, it is highly desirable for an extract based on Olibanum (DAB6 EB6) or Olibanum indicum (Ph.Eur.) to contain both, pentacyclic triterpenoic acids and diterpenic alcohols in appropriate amounts.

In the prior art, a series of *Boswellia* extracts and their respective use were described. For instance, WO 2002/024173 A2 relates to oral dosage forms of *Boswellia* extracts in solid, viscous or liquid form. Said extracts consist of one or more boswellic acids, whose derivatives and blends are produced as gelatin capsules and more effective than tablets. WO 1999/020289 describes highly concentrated plant extracts, suitable for encapsulation into soft gelatin capsules. WO 1996/019212 describes the use of boswellic acids and derivatives for the treatment of brain tumors. An example of a *Boswellia serrata* extract product (ethanol 80% as extraction solvent), which is registered in India and marketed by Gufic Health Care Ltd., Bombay, India, is H 15 Gufic® or Sallaki®.

One potential disadvantage of conventional *Boswellia* extracts is their contents of undesired compounds, such as tannins, allergens or even compounds that were found to be neurotoxic or carcinogenic in an animal model.

In particular, *Boswellia* resins and conventional extracts thereof typically comprise also mono- and sesquiterpenes. As a typical product of terpene producing plants, mono- and sesquiterpenes are regarded as ubiquitous compounds since they have been identified in the volatile oil of many plants (pinene, limonene, linalool, thujon, estragol, cineol, carvon, alpha terpinene, caryophyllene etc.) (Moussaieff et al., Incensole acetate, a novel anti-inflammatory compound isolated from *Boswellia* resin, inhibits nuclear factor-kappa B activation, Mol. Pharmacol. 72(6), 1657-1664; Hamm, S. et al., A chemical investigation by headspace SPME and GC-MS of volatile and semi-volatile terpenes in various olibanum samples. In: Phytochemistry 2005 June; 66(12):1499-1514). Some of these compounds are well known allergens (limonene, linalool), to be neurotoxic in high concentrations (thujone) or even found to be carcinogenic in an animal model, like estragol (Bristol, D. W., NTP technical report on the 3-month toxicity studies of Estragole (CAS no. 140-67-0) administered by gavage to F344/N rats and B6C3F1 mice. NIH publication, no. 11-5966. Toxicity report series, no. 82 (National Toxicology Program (U.S.))). The latter compounds have therefore to be classified as undesired compounds as they might be hazardous for a person ingesting them.

Further compounds found in *Boswellia* resin and resin extracts are pentacyclic triterpenes like amyrin, amyrenes, lupeol, ursene and oleanene (ether soluble neutral lipophilic triterpenes) accounting for roughly 15% (w/w) of the resins. Pentacyclic triterpenes are ubiquitously distributed throughout the plant and characterized by their poor bioavailability (Martinetz, D. et al., Weihrauch and Myrrhe. Stuttgart, 1989; Ching, J. et al., Quantification of α- and β-amyrin in rat plasma by gas chromatography-mass spectrometry: application to preclinical pharmacokinetic study. In: Journal of Mass Spectrometry 2011 May, 46(5):457-464. doi: 10.1002/jms.1912; Hernandez Vázquez, L. et al., The Pentacyclic Triterpenes a, ß-amyrins: A Review of Sources and Biological Activities. In: Rao V. (Ed.): Phytochemicals—A Global Perspective of Their Role in Nutrition and Health. InTech, 2012; Vasconcelos Rodrigues, I. et al., Preparation and In Vitro Evaluation of α and β-Amyrins loaded Nanoemulsions. In: Current Pharmaceutical Biotechnology, 2014, 15(11), DOI: 10.2174/13892010156661403171211647) and could therefore be considered as less important for the unique activity profile of Francincense.

Finally, *Boswellia* resins and extracts thereof usually contain polyphenolic compounds in differing quantities originating from the juice of the bark contaminating the resin during the exudation process of the gum (our own investigations shown in Examples 1, 3, 6, 8, 10 etc. and in Hagers Handbuch der Pharm. Praxis, 3, page 152, 6th edition, 2007 Tannins of catechin-typ and Phlobaphenes). Such protein interacting polyphenolic compounds (e.g. tannins) are well known for a person skilled in the art to interact with proteins, e.g., in the intestinal tract, which may result in reduced resorption of said protein by the intestinal tract, poor tolerability and stomach pain. Further such compounds are incompatible with a high number of pharmaceutical excipients (polyoxyethyleneglykols, polyvinylpyrrolidone, gelatin), since they bind to these excipients and typically form aggregates. In consequence, the use of many common excipients is restricted. Even more critically, the bioavailability of certain desired compounds via the intestinal tract or via the skin is hardly predictable in the presence of said protein interacting phenolic compounds. Depending on the amount of such compounds and their interactions, the bioavailability of one or more of the active components of a *Boswellia* extract may be significantly impaired. Moreover, also from the perspective of unit conformity and batch to batch consistency, said protein interacting polyphenols are to be classified as undesired compounds in a *Boswellia* extract.

In the food industry isinglass, crospovidone and sometimes gelatin is used in quantities of 1-2 g/100 liters of beverage to prevent formation of turbidity caused by tannins crosslinking with dissolved protein in beer and to reduce astringency of wines. However these beverages are highly polar aqueous solutions with a very low amount of alcohol (beer around 4% or wine around 12% (w/w)), which contain only water soluble compounds, mainly sugar, fruit acids, anthocyanines and some minerals (Heiss, R., Lebensmitteltechnologie, pages 380, 381 and 394, 6. Edition, 2004, Springer Verlag, Berlin Heidelberg).

It is therefore an object of the present invention to provide an extract from a resin of a plant of the genus *Boswellia*, which is characterized by both, reduced content of undesired compounds, as well as the presence of desired active ingredients. It is a further object of the present invention to provide a process for preparing such an extract from a resin of a plant of the genus *Boswellia*, wherein the process is suitable for industrial application.

Specifically, it is an object of the present invention to provide an extract, which has a reduced content of undesired compounds, such as limonene (1-Methyl-4-(1-methylethenyl)-cyclohexene; (R)-(+)-limonene (formula Ia); (5)-(−)-limonene (formula Ib)), linalool (3,7-dimethylocta-1,6-dien-3-ol; (5)-(+)-linalool (formula IIa) and (R)-(−)-linalool (formula IIb)), thujone (α: (1S,4R,5R)-4-Methyl-1-(propan-2-yl)bicyclo[3.1.0]hexan-3-one (formula IIIa); β: (1S,4S,5R)-4-methyl-1-propan-2-ylbicyclo[3.1.0]hexan-3-one (formula IIIb)), estragol (1-allyl-4-methoxybenzene; formula IV), while the extract retains desired active compounds, preferably in relative amounts, which correspond approximately to the ratio of the active compounds in the resin. It is thus an object of the present invention to provide an extract from a resin of a plant of the genus *Boswellia*, which has an improved tolerability and toxicity profile and is suitable for use as a food supplement and for use in pharmaceutical and cosmetic compositions.

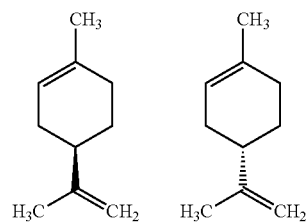

Formula Ia, Ib

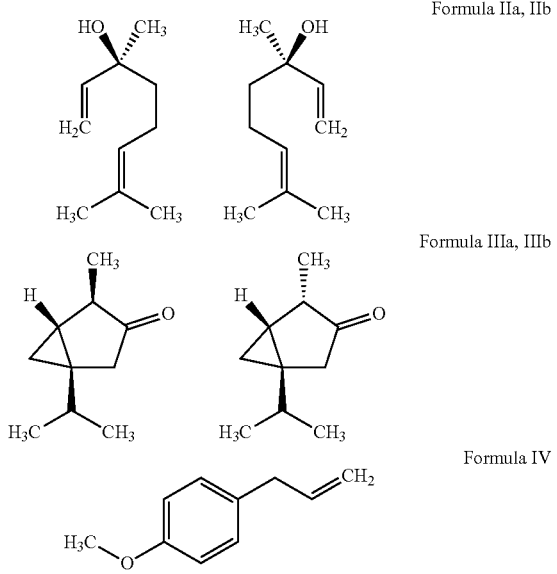

Formula IIa, IIb

Formula IIIa, IIIb

Formula IV

The objectives mentioned above are solved by the present invention, preferably by the subject-matter of the attached claims.

Accordingly, the present invention provides an extract from a resin of a plant of the genus *Boswellia*, wherein the content of at least one compound selected from the group consisting of limonene, linalool, thujone and estragol, and/or the content of at least one compound selected from the group of protein interacting polyphenols, is reduced in comparison to a conventional extract (e.g. a standard ethanolic liquid extract) of the resin. It has surprisingly been found that said extract can be obtained by a novel process, which is industrially applicable. Specifically, the invention concerns an extract from a resin of a plant of the genus *Boswellia*, wherein the content of each of limonene, linalool, thujone is less than 20 ppm and the content of estragol is less than 100 ppm, wherein the content is calculated based on the dry weight of the extract.

Unexpectedly, the extract retains desired active compounds, such as a compound selected from the group of triterpenic acids or derivatives thereof. It has further surprisingly been found that by applying the inventive process it is possible to obtain an extract, which preferably further comprises a compound selected from the group of cyclic, preferably monocyclic, diterpenoids or derivatives thereof, more preferably a cembranoid.

The present invention is based on the unexpected finding that volatile mono- or sesquiterpenoids, such as limonene, linalool, thujone and estragol, as well as polyphenolic compounds can be eliminated from or reduced in an extract from the resin of a plant of the genus *Boswellia*, while the inventive extract retains the content of desired secondary plant metabolites of the plant, preferably a compound selected from the group of triterpenic acids or derivatives thereof. In addition to a compound selected from the group of triterpenic acids and derivatives thereof, the extract according to the invention preferably further contains a compound selected from the group of cyclic diterpenoids or derivatives thereof, preferably a monocyclic diterpenoid, more preferably a cembranoid as defined herein. As it is known that the latter class of compounds does contribute to the beneficial effects of an *Boswellia* extract, the presence of these compounds in the inventive extract represents an important advantage with respect to the use of the extract in the pharmaceutical or cosmetic field as well as with respect to the use of the extract in dietary supplements. Before the present invention, it was not conceivable that a *Boswellia* resin extract could be provided, which is free from undesired (volatile) compounds, but which retains a desired compound selected from the group of cyclic diterpenoids or derivatives thereof, which is typically volatile and thus usually lost in purification processes, such as evaporation and/or distillation. It was even less conceivable that such an extract may be obtained, which has—in addition—a lower content of protein interacting polyphenols.

It has surprisingly been found that the extract according to the invention may preferably comprise a triterpenic acid or a derivative thereof, on the one hand, and a cyclic, preferably a monocyclic, diterpenoid, preferably a cembranoid, or a derivative thereof, on the other hand, in relative amounts, which reflect the relative amounts, i.e. the respective content, in the resin, from which the extract is derived. In particular, the extract according to the invention may comprise a triterpenic acid or a derivative thereof and a cyclic diterpenoid or a derivative thereof in a weight ratio that reflects the ratio that is found in the raw material, i.e. the resin, from which the extract is derived. Without being bound by any theory, it is hypothesized that *Boswellia* owes its beneficial effects, at least in part, to a specific mixture of compounds, comprising, in particular, a triterpenic acid or a derivative thereof as well as a cyclic diterpenoid or a derivative thereof as defined herein. The relative contents of triterpenic acids (and derivatives thereof) and cyclic diterpenoids (and derivatives thereof) in the extract according to the present invention render it particularly suitable for the applications as described herein.

The inventive extract is particularly suitable for pharmaceutical and/or cosmetic applications. In this respect, it is believed that the inventive extract's beneficial effect, in particular in neurodegenerative disease, is due to—at least in part—the advantageous combination of properties of the extract, in particular its anti-inflammatory properties (as illustrated by, for example, downregulation of inflammatory cytokines), its potential vasodilatory and neuroprotective effects (as evaluated, for example, by induction of reactive oxygen species (ROS), such as hydrogen peroxide ($H_2O_2$)). Reactive oxygen species, such as $H_2O_2$, are known to act as powerful vasodilators in cerebral tissue (see, for example, Paravicini T. M. et al. (2004): Increased NADPH-oxidase activity and Nox4 expression during chronic hypertension is associated with enhanced cerebral vasodilation to NADPH in vivo (Stroke 35:584-9)). It has further been suggested that reactive oxygen species mediate neuroprotective effects, which play a role in diverse acute and chronic neurological disorders (see, for example, Huang Y. Z. and McNamara J. O. (2012): Neuroprotective effects of reactive oxygen species mediated by BDNF-independent activation of TrkB. J. Neurosci. 32(44):15521-15532).

Preferably, the weight ratio between the compound selected from the group of triterpenic acids and derivatives thereof and the compound selected from the group of cyclic diterpenoids or derivatives thereof in the extract differs from the weight ratio of the respective compounds in the resin by less than 50%, preferably by less than 35%, more preferably by less than 25%. In other terms, the extract preferably comprises approximately the same or similar (relative) contents of the respective compounds that are present in the resin. Preferably, this holds for the total amounts of the respective compounds extracted from a resin, i.e. the weight ratio between the total amount of the compounds of the group of triterpenic acids and derivatives thereof and the total amount of the compounds of the group of cyclic diterpenoids or derivatives thereof in the extract differs from the weight ratio of the respective total amounts of the respective compound classes in the resin by less than 50%, preferably by less than 35%, more preferably by less than 25%.

Preferably, the inventive extract comprises a compound selected from the group of triterpenic acids or derivatives thereof as defined herein and a compound selected from the group of cyclic, preferably monocyclic, diterpenoids or derivatives thereof as defined herein. More preferably, the content of the compound selected from the group of cyclic diterpenoids or derivatives thereof is at least 4% (w/w), preferably from 10 to 25% (w/w), and wherein the content of the compound selected from the group of triterpenic acids or derivatives thereof is at least 15% (w/w), preferably from 20 to 40% (w/w), wherein the content is calculated based on the dry weight of the extract.

According to a preferred embodiment of the inventive extract, the weight ratio between the compound selected from the group of triterpenic acids or derivatives thereof and the compound selected from the group of diterpenic alcohols or derivatives thereof in the extract differs from the weight ratio of the respective compounds in the resin by less than 50%, preferably by less than 35%, more preferably by less than 25%.

More preferably, the inventive extract comprises a compound selected from the group of cyclic diterpenoids or derivatives thereof, which is selected from the group of cembranoids, preferably from the group consisting of serratol, incensole, iso-incensole, incensole-oxide, iso-incensole-oxide, cembrene A, cembrene C, serratol acetate, incensole acetate, iso-incensole acetate, incensole-oxide acetate and iso-incensole-oxide acetate, and a compound selected from the group of triterpenic acids or derivatives, which is a tetracyclic triterpenic acid or a derivative thereof, or a pentacyclic triterpenic acid or a derivative thereof, more preferably a boswellic acid, a lupeolic acid, a tirucallic acid or a roburic acid.

According to one embodiment, the inventive extract comprises a compound selected from the group of cyclic diterpenoids or derivatives thereof, which is selected from the group of cembranoids, preferably from the group consisting of serratol, incensole, iso-incensole, incensole-oxide, iso-incensole-oxide, cembrene A, cembrene C, serratol acetate, incensole acetate, iso-incensole acetate, incensole-oxide acetate and iso-incensole-oxide acetate, and a compound selected from the group of triterpenic acids or derivatives, which is a boswellic acid, a lupeolic acid, a tirucallic acid or a roburic acid.

Further preferably, the inventive extract comprises a compound selected from the group of cyclic diterpenoids or derivatives thereof, which is selected from the group of cembranoids, preferably from the group consisting of serratol, incensole, iso-incensole, incensole-oxide, iso-incensole-oxide, cembrene A, cembrene C, serratol acetate, incensole acetate, iso-incensole acetate, incensole-oxide acetate and iso-incensole-oxide acetate, and a compound selected from the group of triterpenic acids or derivatives, which is preferably a boswellic acid.

As used herein, the term 'extract' refers to a mixture of compounds, which is obtained from a resin of a plant of the genus *Boswellia* by using a suitable extraction procedure. In this context, the extract may be a liquid extract (e.g. an oily extract), a semi-solid extract (e.g. a waxy extract) or, if—for instance—all solvents and liquid components have been evaporated, a dry extract (e.g. a powder). An extraction procedure in the meaning of the present invention may be any procedure employing a solvent for extracting a certain compound or, more typically, a mixture of compounds from a plant raw material, more specifically, a resin of a plant of the genus *Boswellia*. Mechanical means (e.g. milling, agitating or the like) and/or temperature changes (such as heating, freeze-thaw cycles) are typically further used during extraction. In the context of the present invention, the term 'extract' typically refers to the extract according to the present invention or to the final product of the process according to the invention, respectively. The term 'extract' as used herein thus typically refers to a purified extract, unless otherwise specified. For instance, the term 'extract' is used herein with respect to the product obtained in the final step according to the present invention. Intermediate products are referred to herein as, for example, 'unpurified extract', 'raw extract', 'native extract', 'conventional extract', 'standard extract' or 'standard ethanolic liquid extract'. The latter terms may be used in the context of the present invention with regard to the extraction solution obtained after a first extraction step, wherein the first extraction step typically does not comprise specific purification steps. Thus, the terms 'unpurified extract', 'raw extract', 'native extract', 'conventional extract', 'standard extract' or 'standard ethanolic liquid extract' as used herein concern the liquid, which is obtained by a single extraction step, which comprises contacting the resin with a solvent, preferably an organic solvent, incubating the resin with the solvent (e.g. by agitating and heating the mixture) and separating the insoluble components from the extraction solution by one or more separation steps, preferably selected from the group consisting of centrifugation and filtration. As used herein, an 'unpurified extract' may thus preferably be a conventional extract, such as a standard ethanolic liquid extract, of a resin of a plant of the genus *Boswellia*, which may be an intermediate of the process according to the present invention, preferably as obtained, for example, in Examples 1, 3 or 6 as described herein.

The extract according to the invention is characterized, amongst other criteria, by its contents of limonene, linalool, thujone and estragol. Furthermore, the extract according to the invention is preferably characterized by its contents of a compound selected from the group of protein interacting polyphenols. Moreover, the extract is preferably characterized by its contents of a compound selected from the group of triterpenic acids and derivatives thereof, as defined herein, and/or its contents of a compound selected from the group of cyclic, preferably monocyclic, diterpenoids or derivatives thereof.

The present invention preferably provides an extract, which typically comprises a reduced relative amount of at least one essential oil as compared to a conventional extract. Preferably, the sum of the relative amounts of essential oils comprised in the inventive extract is reduced with respect to the sum of relative amounts of essential oils comprised in a conventional extract.

According to a preferred embodiment, the relative amount of essential oils is reduced in the inventive extract in comparison to the resin, from which it is derived. More preferably, the relative amount of one or more essential oils in the inventive extract is reduced with respect to the resin, from which the extract is derived. Preferably, the sum of the relative amounts of essential oils comprised in the inventive extract is reduced with respect to the sum of relative amounts of essential oils comprised in the resin, from which the extract is prepared.

According to a preferred embodiment, the invention provides an extract that has been purified from undesired essential oil components, preferably by evaporation or distillation. In the context of the present invention, the term 'essential oil' refers to a volatile compound or to a mixture of volatile compounds, which typically contribute to the plant's fragrance. As used herein, the term 'essential oil' also refers to a volatile compound or a mixture of volatile compounds, which are part of a concentrated hydrophobic liquid containing volatile aroma compounds from a plant, preferably a plant of the genus Boswellia as defined herein. An 'essential oil' as used herein is essential in the sense that it contains the essence of a plant's fragrance, so that the characteristic fragrance of the plant, from which it is derived, is determined or influenced by the essential oil. An essential oil is generally extracted by evaporation or distillation, preferably by using steam. Other processes suitable for isolation of an essential oil from a plant raw material, such as a resin, include expression or solvent extraction. The present invention advantageously provides an extract (and a process for preparing that extract), which is characterized in that it preferably comprises a relative amount of one or more essential oils, preferably as defined herein, which is reduced in comparison to the respective relative amount(s) in the resin, from which the extract is derived.

In particular, the content in the inventive extract of each of limonene, linalool and thujone is less than 20 ppm, and the content of estragol is less than 100 ppm, wherein the content is calculated based on the dry weight of the extract. According to a particularly preferred embodiment, the invention relates to an extract as defined herein, wherein the content in the inventive extract of each of limonene, linalool and thujone is less than 20 ppm, and the content of estragol is less than 100 ppm, wherein the content is calculated based on the dry weight of the extract, and wherein furthermore the relative amount(s) of one or more other essential oils, preferably as defined herein, more preferably the sum of the relative amounts of essential oils, is further reduced in comparison to a conventional extract. Preferably, the relative amount of at least one essential oil (other than limonene, linalool, thujone and estragol) is reduced in comparison with the respective relative amount in the resin, from which the extract is derived. More preferably, the sum of the relative amounts of essential oils in the extract is reduced with respect to the sum of the relative amounts of essential oils in the resin, from which the extract is derived.

In the context of the present invention, the term 'essential oil' preferably comprises a hydrophobic liquid, more preferably a concentrated hydrophobic liquid, containing a volatile compound or a mixture of volatile aroma compounds, such as monoterpene compounds, sesquiterpene compounds or phenylpropanoid compounds, which are isolated from a plant raw material, for example, by distillation or steam distillation.

In a preferred embodiment, the term 'essential oil', as used herein, relates to a monoterpene compound, a sesquiterpene compound or a phenylpropanoid compound, preferably as defined herein. A monoterpene compound as used herein is preferably an acyclic, monocyclic or bicyclic monoterpene compound. In this context, an acyclic monoterpene compound is preferably selected from ocimene, myrcene, geraniol, citral, citronellal, citronellol, linalool, or others. A monocyclic monoterpene compound is preferably selected from limonene, phellandrenes, p-cymene, menthol, thymol, carvacrol or others. A bicyclic monoterpene compound is preferably selected from carene, sabinene, camphene, thujene, thujone, camphor, borneol or others. A sesquiterpene compound, as used herein, is preferably an acyclic, monocyclic or multicyclic compound. In a preferred embodiment, a sesquiterpene compound is selected from farnesene, farnesol, humulene, caryophyllene, guaiazulene, longifolene, copaene, patchoulol or others. Phenylpropanoids are a diverse family of organic compounds that are synthesized by plants from the amino acid phenylalanine. In the context of the invention, a phenylpropanoid compound is preferably derived from a coniferyl alcohol, more preferably from an intermediate coniferyl alcohol. More preferably, a phenylpropanoid compound as used herein is preferably selected from eugenol, chavicol, safrole estragole, anethole, apiole or others.

The contents of said compounds in the extract according to the invention is defined herein as calculated based on the dry weight of the extract. In other words, the contents of one or more of said compounds in the inventive extract may be determined, for example, in 'ppm' or 'percent (w/w)'. To this end, a given volume of the extract may be analysed by using one or several techniques known in the art (e.g. by chromatography, MS). The thus determined amount of a compound of interest is then calculated based on the weight of the dry residue (e.g. a solid content after evaporation) of the corresponding volume of the extract. The 'dry weight of the extract' as used herein is thus most readily obtained in the case of an extract according to the invention, if said extract is provided in a form, of which a completely dry form may be obtained by using a procedure (e.g. evaporation) that eliminates any volatile compounds (especially solvents, such as an organic solvent or water), while leaving the desired ingredients, preferably the desired compounds as defined herein, intact. Typically, the dry weight of the extract is the weight of the extract, which is completely free of water and solvent (e.g. after evaporation). Preferably, the dry weight of the extract is the weight of the dried residue of an extract, wherein the residue comprises essentially only components derived from a resin of a plant of a genus Boswellia.

In some cases (e.g. in an extract comprising a highly hydrophobic phase or in an extract comprising an oily phase), it may not be feasible to obtain the dried residue of an extract, at least not while leaving the ingredients intact. In the context of the present invention, the content of a compound of interest (such as limonene, linalool, thujone, estragol, a polyphenol, a triterpenic acid or a diterpenoid) in such an extract may nevertheless be specified 'as calculated based on the dry weight of the extract'. Accordingly, the amount of said compound of interest (preferably in 'ppm' or '% w/w') is determined by known analytical methods. The content of said compound of interest is then calculated based on the weight of the dry residue of the last intermediate in the process, for which the dry weight can be obtained (e.g. by evaporation). For instance, said last intermediate may be a purified ethanolic liquid extract (cf. Examples 4, 7 or 11). For example, if the inventive (liquid, semi-solid or dry) extract is derived from 100 ml of a purified ethanolic liquid extract, the amount (i.e. the weight) of one or more of said compounds in the inventive extract is determined by a method known to the person skilled in the art. The content of the inventive extract is then calculated based on the dry weight of 100 ml of the respective purified ethanolic liquid extract, from which the extract according to the invention is derived.

According to the invention, the extract is derived from a resin of a plant of the genus Boswellia (Burseraceae).

Typically, the extract is derived from a resin of a *Boswellia* species, which is characterized by its contents of a compound selected from the group of triterpenic acids or derivatives thereof, preferably a boswellic acid or a derivative thereof, as defined herein. Preferably, the plant further comprises also a compound selected from the group of cyclic diterpenoids or a derivative thereof, preferably a monocyclic diterpenoid or a derivative thereof as described herein. Examples of plants of the genus *Boswellia* in the meaning of the invention comprise, but are not limited to, *Boswellia papyrifera*, *Boswellia serrata*, *Boswellia sacra* and *Boswellia carterii*. While the term *Boswellia sacra* refers to the South-Arabian plant (Oman, Yemen) and the term *Boswellia carteri* refers to the Somalian plant, the two species are sometimes regarded as the same based on taxonomic criteria.

Preferably, the expression "a plant of the genus *Boswellia*" as used herein relates to a plant selected from the group consisting of *Boswellia papyrifera*, *Boswellia serrata*, *Boswellia sacra* and *Boswellia carterii*. More preferably, the expression relates to a plant of the genus *Boswellia*, which is preferably not *Boswellia papyrifera*. Furthermore, the expression "a plant of the genus *Boswellia*" in the context of the present invention preferably relates to *Boswellia serrata*.

In the context of the present invention, the term 'resin' refers to a mixture of several organic compounds, which is obtained as an exudate from a plant of the genus *Boswellia*. The resin is typically obtained by incising the stem or a branch of a plant of the genus *Boswellia*, upon which the resin leaks from the site of the injury. A resin of a plant of the genus *Boswellia*, is usually a viscous liquid or semi-solid, which (depending, amongst other factors, on the ambient temperature) solidifies when it is exposed to air. Accordingly, the resin is typically harvested by collecting the solidified material from the sites on a *Boswellia* plant, where a cut has earlier been made. For instance, two weeks after introducing a cut in a plant of the genus *Boswellia*, the solidified resin may be harvested, e.g. by scratching off the material from the injury site(s). In order to obtain the extract according to the invention, a resin of a plant of the genus *Boswellia* may be directly used as raw material. Alternatively, the resin may be e.g. mechanically, thermally or chemically processed (for instance, by milling, freeze-drying or the like) prior to extraction. Accordingly, the resin, from which the extract of the present invention is derived, may also be a processed resin of a plant of the genus *Boswellia*. Preferably, a resin is used as a starting material, which has a mean particle size of less than 5 mm, more preferably less than 4 mm, 3 mm, 2 mm or 1 mm. Most preferably, the resin has a meant particle size of less than 2 mm.

In a preferred embodiment, the extract according to the invention is derived from a resin from a plant of the genus *Boswellia*, preferably as defined herein. More preferably, the extract is derived from a resin from a plant of the genus *Boswellia*, which is not *Boswellia papyrifera*. Most preferably, the extract is derived from a resin from *Boswellia serrata*.

The extract from a resin of a plant of the genus *Boswellia* according to the invention is characterized in that it comprises reduced amounts of undesired terpenic compounds or derivatives thereof in comparison with a conventional extract from the same resin. Specifically, the amount of at least one compound selected from the group consisting of limonene (see formula Ia, Ib), linalool (see formula IIa, IIb), thujone (see formula IIIa, IIIb) and estragol (see formula IV) is reduced. In the context of the present invention, the term 'limonene' refers to a compound as illustrated by formulas Ia or Ib herein (1-Methyl-4-(1-methylethenyl)-cyclohexene; (R)-(+)-limonene (formula Ia); (S)-(−)-limonene (formula Ib)). The term 'linalool' refers to a compound as illustrated by formula IIa or IIb herein (3,7-dimethylocta-1,6-dien-3-ol; (S)-(+)-linalool (formula IIa) and (R)-(−)-linalool (formula IIb)). The term 'thujone' refers to a compound illustrated by formula IIIa or IIIb herein (a: (1S,4R,5R)-4-Methyl-1-(propan-2-yl)bicyclo[3.1.0]hexan-3-one (formula IIIa); 13: (1S, 4S,5R)-4-methyl-1-propan-2-ylbicyclo[3.1.0]hexan-3-one (formula IIIb)). The term 'estragol' refers to a compound as illustrated by formula IV herein (1-allyl-4-methoxybenzene; formula IV). Moreover, the terms 'limonene', 'linalool', 'thujone' and 'estragol' do not only comprise the enantiomers of the respective compounds, but further comprise also any derivative of said compounds. The presence of terpenic compounds in the extract and their respective amounts are readily determined by methods known in the art, e.g. by using chromatography (for instance, gas chromatography or HPLC) coupled to a mass spectrometry (MS) readout.

Preferably, the content of at least one of these compounds in the extract is less than 50% (w/w) of the content of the same compound in a conventional extract from the same resin as defined herein, more preferably, less than 40% (w/w), even more preferably less than 30% (w/w), most preferably less than 25% (w/w), wherein the content is calculated based on the dry weight of the extract as described herein.

In a certain embodiment, the total content of the compounds limonene (see formula Ia, Ib), linalool (see formula IIa, IIb), thujone (see formula IIIa, IIIb) and estragol (see formula IV) is reduced with respect to a conventional extract from the same resin. Preferably, the total content of these compounds in the extract according to the invention is less than 50% (w/w) of the total content of the compounds in a conventional extract from the same resin, more preferably, less than 40% (w/w), even more preferably less than 30% (w/w), most preferably less than 25% (w/w).

In a preferred embodiment, the content of each of limonene (see formula Ia, Ib), linalool (see formula IIa, IIb), thujone (see formula IIIa, IIIb) and estragol (see formula IV) is reduced in the extract according to the present invention. Preferably, the content of each of these compounds in the extract is less than 50% (w/w) of the content of the respective compound in a conventional extract from the same resin, more preferably, less than 40% (w/w), even more preferably less than 30% (w/w), most preferably less than 25% (w/w).

Preferably, the content of at least one compound selected from the group consisting of limonene, linalool, thujone and estragol in the extract according to the invention is less than 100 ppm, preferably less than 90, 80, 70, 60 or 50 ppm, more preferably less than 20 ppm, most preferably less than 10 ppm. More preferably, the content of each of limonene, linalool, thujone and estragol in the extract according to the invention is less than 200 ppm, preferably less than 150, 100, 90, 80, 70, 60 or 50 ppm, more preferably less than 20 ppm, most preferably less than 10 ppm. Even more preferably, the content of each of limonene, linalool, thujone is less than 20 ppm and the amount of estragol is less than 100 ppm, wherein the content is calculated based on the dry weight of the extract. Most preferably, the content of linalool is less than 20 ppm, the content of each of limonene and thujone is less than 10 ppm and the amount of estragol is less than 100 ppm.

The extract according to the invention is further characterized in that it contains a reduced amount of at least one compound selected from the group of polyphenols, preferably from the group of protein interacting polyphenols, as compared to a conventional extract from the same resin.

The term 'polyphenol' (or 'polyphenolic compound'), as used herein, generally refers to an organic compound characterized by the presence of multiples of phenol structure units or a derivative of such a compound. In the context of the present invention, the term 'polyphenol' further comprises compounds as defined according to the definition proposed by Stéphane Quideau, i.e. to any compound, which is exclusively derived from the shikimate/phenylpropanoid and/or the polyketide pathway, featuring more than one phenolic unit and deprived of nitrogen-based functions. Specifically, the term refers to compounds as defined above, which are typically secondary metabolites of plant origin and are contained in the resin of a plant of the genus *Boswellia*. Polyphenol compounds frequently contain a multitude of repeating phenolic moieties of smaller molecules (e.g. pyrocatechol, resorcinol, pyrogallol or phloroglucinol), which may originate from various biosynthetic pathways. Plant polyphenols are sometimes classified into two large groups, proanthocyanidins (or condensed, non-hydrolysable tannins) on the one hand and polyesters (or hydrolysable tannins) on the other hand, both of which are encompassed by the term 'polyphenol' as used herein. Proanthocyanidins are typically large molecules of up to 20.000 Da, which are composed of catechin units and exist as oligomers and polymers, where solubility usually decreases with increasing polymer length. Polyesters or hydrolysable tannins are usually molecules of up to 3.000 Da, which are based on gallic and/or hexahydroxydiphenic acid and their derivatives. A resin from a plant of the genus *Boswellia* usually contains a mixture of polyphenolic compounds as defined herein, such as tannins (e.g. of the catechin-type) and/or derivatives thereof (e.g. phlobaphenes). Amongst the polyphenols that have been identified in the resin of a plant of the genus *Boswellia*, at least some are known to interact with proteins or peptides, which are comprised in the phrase 'protein interacting polyphenol' as used herein.

The phrase 'protein interacting polyphenol', in the context of the present invention, refers to a polyphenol as defined herein, which interacts with a protein, a peptide or a protein moiety (or peptide moiety, respectively) of a compound comprising a protein or peptide moiety and a non-protein/non-peptide moiety. A protein interacting polyphenol typically has the capacity to form a complex with a protein or peptide (or a protein or peptide moiety). The formation of such a protein-polyphenol complex typically leads to precipitation of the complex from a solution (depending on the solvent). According to one hypothesis, a protein interacting polyphenol acts as a multidentate ligand, which—through different phenolic groups—binds simultaneously to different sites on the protein. The interaction between a protein interacting polyphenol and a protein or peptide is typically based on noncovalent interactions, such as hydrogen bonds or hydrophobic interaction. Under certain conditions, covalent linkages may also be established between a protein interacting polyphenol and a protein or peptide. Accordingly, the term 'protein-polyphenol-complex' as used herein refers to a compound selected from the group of protein interacting polyphenols as defined herein, which interacts with a protein or peptide as defined herein.

The protein interacting polyphenols in the meaning of the present invention may also interact with a synthetic polymer, preferably an insoluble synthetic polymer as defined herein. Analogously to the process described above with respect to the interaction between polyphenol and protein, the interaction between a protein interacting polyphenol and a synthetic compound may thus lead to the formation of insoluble complexes.

Protein interacting polyphenols play an important role as contaminants of *Boswellia* resins. Conventional extracts from a resin of a plant of the genus *Boswellia* usually contain considerable amounts of protein interacting polyphenols, which are considered as undesired compounds as they may interfere with other ingredients of the extract (e.g. rendering said ingredients ineffective and/or inhibiting their resorption in the intestinal tract) or even cause undesirable side-effects (e.g. stomach pain), when the extract is used by a subject. In particular, tannins and derivatives thereof (e.g. phlobaphenes) have been identified in conventional extracts of a plant of the genus *Boswellia*.

As used herein, the term 'tannin' refers to a certain class of polyphenolic compounds comprised in a resin of a plant of the genus *Boswellia* that readily interact with a protein or a peptide. More specifically, the term relates to hydrolysable (monomer: gallic acid or a derivative thereof) and non-hydrolysable tannins (proanthocyanidins; monomer: flavone or a derivative thereof, e.g. a catechin). Preferably, a tannin in the meaning of the present invention comprises at least twelve hydroxyl groups and at least five phenyl groups.

With respect to the precipitation of the protein-polyphenol complex, which is formed by interaction of a protein interacting polyphenol with a protein, a peptide or a protein moiety (or peptide moiety, respectively) of a compound comprising a protein or peptide moiety and a non-protein/non-peptide moiety, in theory two scenarios can be envisaged:

At low (relative) protein or peptide concentrations, a protein interacting polyphenol interacts with one or more sites on the surface of the protein or peptide to form a layer surrounding the protein or peptide, which is less hydrophilic than the protein or peptide. Depending on the conditions (in particular, the solvent), this leads to precipitation of the protein-polyphenol complex.

At high (relative) protein or peptide concentrations, a single protein interacting polyphenol may interact with more than one protein or peptide molecule (via interaction of different phenolic moieties of the protein interacting polyphenol with different protein or peptide molecules). Under these conditions, the protein interacting polyphenol acts as a 'crosslinker' between the protein or peptide molecules. Aggregates are formed that are less hydrophilic than the protein or peptide itself and thus precipitate.

According to the present invention, an extract from a *Boswellia* resin is provided, wherein the total content of polyphenols, preferably protein interacting polyphenols, in the extract is reduced in comparison to a conventional extract from the same resin. Preferably, the total content of polyphenols, preferably protein interacting polyphenols, in the extract is less than 0.10% (w/w), more preferably less than 0.09%, 0.08%, 0.07%, 0.06% or 0.05% (w/w). Most preferably, the extract according to the invention does not comprise detectable amounts of a polyphenolic compound.

Preferably, the amount of at least one compound selected from the group of protein interacting polyphenols as defined herein is reduced in comparison to the amount in a conventional extract from the same resin. In a preferred embodiment, the at least one compound selected from the group of protein interacting polyphenols is a tannin, which is preferably selected from hydrolysable and non-hydrolysable tannins. More preferably, the extract according to the invention comprises a reduced amount of a tannin of the catechin-type as compared to a conventional extract.

The extract according to the present invention furthermore preferably comprises a compound selected from the group of triterpenic acids or derivatives thereof.

The phrase 'triterpenic acids or derivatives thereof' as used herein, generally refers to compounds having a molecular skeleton comprising 30 C-atoms, which is composed of six isoprene units. In the context of the present invention, the phrase relates to such compounds as defined above, which typically have one or more carboxyl groups, as well as to structural derivatives thereof, such as esters of a triterpenic acid with another compound. For instance, a carboxyl group of a triterpenic acid can react with a hydroxyl group of an alcohol in order to form an ester. Preferably, a derivative of a triterpenic acid may be formed by reaction of a triterpenic acid with a $C_1$ to $C_6$ alcohol, preferably with methanol, ethanol or propanol. More preferably, a hydroxyl group of a triterpenic acid may react with a carboxyl group of an organic acid in order to form an ester. Preferably, a derivative of a triterpenic acid may be formed by reaction of a triterpenic acid with formic acid or acetic acid.

Preferably, the extract according to the invention comprises a compound selected from the group of triterpenic acids or derivatives thereof, which is a pentacyclic triterpenic acid or a derivative thereof, more preferably a boswellic acid or a derivative thereof or a lupeolic acid or a derivative thereof. In a particularly preferred embodiment, the extract according to the present invention comprises a boswellic acid, preferably an α-boswellic acid, a β-boswellic acid, an acetyl-boswellic acid or a keto-boswellic acid. More preferably, the extract comprises a boswellic acid selected from the group consisting of α-boswellic acid, β-boswellic acid, acetyl-α-boswellic acid, acetyl-β-boswellic acid, 11-keto-β-boswellic acid (KBA) and acetyl-11-keto-β-boswellic acid (AKBA).

In addition or alternatively, the extract according to the invention preferably also comprises a compound selected from the group of triterpenic acids or derivatives thereof, which is a tetracyclic triterpenic acid or a derivative thereof, more preferably a tirucallic acid or a derivative thereof or a roburic acid or a derivative thereof. Therein, the tirucallic acid is preferably selected from the group consisting of 3-α-acetoxytirucall-8,24-dien-21-acid, 3-α-hydroxytirucall-8,24-dien-21-acid, 3-β-hydroxytirucall-8,24-dien-21-acid, 3-ketotirucall-8,24-dien-21-acid and 3-oxo-tirucallic acid.

The extract according to the invention preferably comprises a compound selected from the group of triterpenic acids or derivatives thereof as defined herein, preferably a compound selected from the group of pentacyclic triterpenic acids or derivatives thereof and tetracyclic triterpenic acids or derivatives thereof, wherein the content of said compound is at least 10 (w/w), preferably at least 15% (w/w), more preferably at least 20% (w/w). Alternatively, the content of a compound selected from the group of triterpenic acids or derivatives thereof as defined herein is preferably in the range from 10 to 60% (w/w), more preferably from 15 to 50% (w/w), even more preferably from 20 to 40% (w/w).

In a preferred embodiment, the extract according to the invention comprises a compound selected from the group of cyclic diterpenoids or derivatives thereof.

In the context of the present invention, the phrase 'cyclic diterpenoids or derivatives thereof' generally refers to cyclic compounds having a molecular skeleton comprising 20 C-atoms, which is composed of four isoprene units. In the context of the present invention, the phrase 'cyclic diterpenoids or derivatives thereof' comprises a monocyclic diterpenoid, in particular a monocyclic diterpenic alcohol or a derivative thereof. In the context of the present invention, a monocyclic diterpenic alcohol is a monocyclic diterpenoid comprising at least one hydroxyl group or a derivative thereof. The term 'cyclic diterpenoids or derivatives thereof' also comprise monocyclic diterpenic alcohols or derivatives thereof, such as an acetate of a monocyclic diterpenic alcohol. The phrase 'cyclic diterpenoids or derivatives thereof' as used herein more specifically comprises cembranoids or derivatives thereof.

In the context of the present invention, the term 'cembranoids' refers to monocyclic diterpenoids, which comprise a ring of 14 C-atoms. The term 'cembranoids', as used herein, comprises unsaturated cyclotetradecane derivatives. More specifically, the term 'cembranoids' also comprises cembrenes and derivatives thereof, such as serratol, incensole, iso-incensole, incensole-oxide, iso-incensole-oxide, cembrene A and cembrene C, serratol acetate, incensole acetate, iso-incensole acetate, incensole-oxide acetate and iso-incensole-oxide acetate.

Typically, cyclic diterpenoids are volatile compounds, which are frequently lost during extract preparation due to evaporation. However, cyclic diterpenoids and derivatives thereof comprise compounds, which have beneficial effects and are thus considered as desirable compounds in a *Boswellia* resin extract.

Preferably, the extract according to the invention comprises a compound selected from the group of monocyclic diterpenoids, preferably a monocyclic diterpenic alcohol or a derivative thereof. More preferably, the extract comprises an acetate of a monocyclic diterpenic alcohol.

Preferably, the extract according to the invention comprises a cembranoid or a derivative thereof, preferably as defined herein. More preferably, the extract comprises a compound selected from the group of cembrenes or derivatives thereof. More preferably, the extract comprises an acetate of a compound selected from the group of cembranoids or derivatives thereof, preferably an acetate of a cembrene.

In a particularly preferred embodiment, the extract according to the invention comprises a compound selected from the group of cyclic, preferably monocyclic, diterpenoids, wherein the compound is preferably selected from the group consisting of serratol, incensole, iso-incensole, incensole-oxide, iso-incensole-oxide, cembrene A and cembrene C, serratol acetate, incensole acetate, iso-incensole acetate, incensole-oxide acetate and iso-incensole-oxide acetate.

Preferably, the compound selected from the group of cyclic diterpenoids or derivatives thereof, preferably a monocyclic diterpenoid as defined herein or a derivative thereof, more preferably a compound from the group of cembranoids as defined herein or a derivative thereof, is present in the extract according to the invention in a content of at least 1%, 2%, 3%, 4%, 5%, 6%, 7%, 8%, 9%, 10% or 15% (w/w), preferably in a content in a range from 5 to 40%, 7 to 30%, or 10 to 25% (w/w). Preferably, the compound selected from the group of cyclic diterpenoids or derivatives thereof, preferably a monocyclic diterpenoid as defined herein or a derivative thereof, more preferably a compound from the group of cembranoids as defined herein or a derivative thereof, is present in a content of at least 4 (w/w), preferably in a content from 10 to 25% (w/w).

In a preferred embodiment, the extract according to the invention comprises both, a compound selected from the group of triterpenic acids or derivatives thereof as defined herein, as well as a compound selected from the group of cyclic diterpenoids, preferably monocyclic diterpenoids, or derivatives thereof as defined herein. Preferably, the compounds are present in the extract in a content as defined herein. More preferably, the extract according to the invention comprises a triterpenic acid or a derivative thereof, on the one hand, and a monocyclic diterpenoid, preferably a monocyclic diterpenic alcohol or a cembranoid, or a derivative thereof, on the other hand, in relative amounts, which reflect the relative amounts in the resin, from which the extract is derived. In particular, the extract according to the invention may comprise triterpenic acids and derivatives thereof and cyclic, preferably monocyclic, diterpenoids and derivatives thereof in a weight ratio that reflects the weight ratio that is found in the raw material, i.e. the resin, from which the extract is derived.

Preferably, the weight ratio between the compound selected from the group of triterpenic acids and derivatives thereof and the compound selected from the group of cyclic diterpenoids or derivatives thereof in the extract differs from the weight ratio of the respective compounds in the resin by less than 50%, preferably by less than 35%, more preferably by less than 25%. In other terms, the extract comprises approximately the same or similar (relative) amounts of the respective compounds that are present in the resin. Preferably, this holds for the total amounts of the respective compounds, i.e. the weight ratio between the total amount of the compounds of the group of triterpenic acids and derivatives thereof and the total amount of the compounds of the group of cyclic diterpenoids or derivatives thereof in the extract differs from the weight ratio of the respective total amounts of the compounds of the respective compound classes in the resin by less than 50%, preferably by less than 35%, more preferably by less than 25%.

Preferably, the extract according to the present invention comprises a compound selected from the group of cyclic diterpenoids or derivatives thereof, preferably a monocyclic diterpenoid, more preferably a monocyclic diterpenic alcohol or a derivative thereof, even more preferably a compound from the group of cembranoids as defined herein, which is present in a content of at least 4% (w/w), preferably in a content from 10 to 25% (w/w), and further comprises a compound selected from the group of triterpenic acids or derivatives thereof, which is present in a content of least 15% (w/w), preferably in a content from 20 to 40% (w/w).

The extract according to the invention is preferably liquid or semi-solid. In this context, the term 'liquid' refers to an extract, which readily flows, preferably comparable to a solvent such as water or a more viscous liquid, such as an oil. The term 'semi-solid' refers to an extract, which is not solid, but rather amorphous. Typically, a semi-solid extract as used herein is an extract that is characterized by a considerable degree of viscosity. Preferably, the extract is an oily extract, which may be liquid or semi-solid. Preferably, the extract according to the invention is semi-solid extract, that does not flow freely (in contrast to the liquid extract), but is not solid and may change its shape, e.g. under pressure. Preferably, the extract changes its behavior depending on the temperature. For instance, the extract may be a waxy or semi-solid oily extract at room temperature, while it is a liquid extract at, for example, 37° Celsius. The extract is preferably an oily liquid extract or an oily semi-solid extract. In the context of the present invention, the term 'oily extract' comprises liquid or semi-solid extracts. The term 'oily extract', as used herein, may also refer to waxy extracts.

The pH value of the inventive extract is preferably in a range from 3 to 10, more preferably in a range from about 3.5 to about 8, even more preferably in a range from about 4 to about 7. According to a preferred embodiment, the pH value of the inventive extract is about 7 or less. More preferably, the pH value of the inventive extract is in a range from about 5 to about 6.

Alternatively, the extract according to the invention is solid. Preferably, the extract is provided in the form of a powder or a granulate, preferably a dry powder or a dry granulate.

Preferably, the pH value of the solid or dry extract upon reconstitution in deionized water is as described herein. Most preferably, the pH value of the solid or dry extract upon reconstitution in deionized water is about 7 or less.

In another aspect, the present invention provides a process for preparing an extract from a resin of a plant of the genus *Boswellia*. Advantageously, the process according to the present invention is suitable for preparation of a *Boswellia* resin extract, wherein desired compounds, such as a compound selected from the group of triterpenic acids or derivatives thereof and/or a compound selected from the group of cyclic, preferably monocyclic, diterpenoids as defined herein or derivatives thereof, are isolated and, preferably, enriched in the extract, whereas undesired compounds as defined herein are not present in the extract or present only in reduced amounts with respect to a conventional extract. The process according to the present invention is thus particularly suitable for preparing an extract, which—due to excellent efficacy and improved tolerability and safety—may be used in pharmaceutical or cosmetic compositions as well as in a food or a food supplement.

More specifically, the present invention concerns a process for preparing an extract from a resin of a plant of the genus *Boswellia*, wherein the content in the extract of at least one compound selected from the group consisting of limonene, linalool, thujone and estragol, and/or the amount of at least one compound selected from the group of protein interacting polyphenols, is reduced in comparison to a conventional extract of the same resin, the process comprising the steps of:

a) contacting the resin with an extraction solvent to obtain an extraction solution, wherein the extraction solvent comprises a first organic solvent miscible with water, or a supercritical fluid, or a mixture thereof;
b) separating insoluble components from said extraction solution,
c) concentrating said extraction solution by evaporation and/or distillation,
d) optionally adding a lipid phase,
e) concentrating the obtained extraction solution by distillation and/or evaporation;
f) purification of the obtained concentrate by adding water and distillation, followed by evaporation and finally obtaining a dry extract, or,
   if a lipid phase was added in step d), obtaining a liquid or semi-solid extract.

Therein, the starting material is a resin or a processed resin as described herein from a plant of the genus *Boswellia* as described herein. Preferably, the resin is derived from a plant selected from the group consisting of *Boswellia papyrifera*, *Boswellia serrata*, *Boswellia sacra* and *Boswellia carterii*.

In a preferred embodiment, the resin is derived from a plant of the genus *Boswellia*, which is not *Boswellia papyrifera*. Most preferably, the resin is derived from a resin from *Boswellia serrata*.

The process according to the invention involves a step of contacting the resin with an extraction solvent in order to obtain an extraction solution, wherein the extraction solvent is a first organic solvent miscible with water, or a supercritical fluid, or a mixture thereof.

Therein, the resin, which is contacted with an extraction solvent, is preferably prepared or processed beforehand as described herein. For instance, the resin may be milled, sieved, washed, heated, frozen, treated by freeze-and-thaw cycles, humidified or soaked in water prior to contacting it with the extraction solvent. The particle size of the resin, which is used as starting material, is preferably in the range from 0.01 mm to 8 mm, more preferably below 5 mm, 4 mm, 3 mm, 2 mm or 1 mm. Most preferably, the particle size of the resin is below 2 mm. Alternatively, a powder having an even smaller particle size may be used.

The term 'contacting' according to the present invention preferably refers to wetting, submerging, bathing or any type of incubation of the resin with an extraction solvent. Preferably, the mixture of resin and extraction solvent is incubated before proceeding to step b) of the process. The incubation is preferably carried out at a temperature in the range from 10 to 90 degrees Celsius, more preferably from 20 to 80 degrees Celsius, even more preferably from 30 to 70 degrees Celsius, most preferably from 40 to 60 degrees Celsius.

Preferably, the incubation in step a) of the process lasts for at least 5 minutes, 15 minutes, 30 minutes, 60 minutes or 90 minutes, more preferably in the range from 10 to 90 minutes, even more preferably in the range from 30 to 80 minutes. During incubation, the mixture is preferably agitated, wherein the term 'agitation' refers to mechanically moving, shaking or stirring of the resin material in the mixture, e.g. by a stirring bar, a stirring rod or by means of an agitator. Agitator devices are known to the skilled person and may be readily obtained from commercial sources.

The extraction solvent comprises a first organic solvent miscible with water or a mixture of a first organic solvent miscible with water. Preferably, the (first and/or second) solvent miscible with water is selected from the group consisting of acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran and triethylene glycol. In a preferred embodiment of the process according to the present invention, the (first and/or second) solvent miscible with water is an alcohol, such as for example any of methanol, ethanol, isopropanol, aromatic alcohols, preferably ethanol or methanol, most preferably ethanol. Most preferably, the extraction solvent comprises a mixture of water and the first organic solvent miscible with water as defined herein, preferably a mixture of water and alcohol, more preferably a mixture of water and an alcohol selected from the group consisting of methanol, ethanol, isopropanol or an aromatic alcohol, more preferably ethanol or methanol, or a mixture of water and ketone, preferably acetone. Preferably, the extraction solvent is an ethanol/water mixture.

In a more preferred embodiment the extraction solvent in the process according to invention is an alcohol, preferably ethanol, in a concentration of at least about 50% (w/w) to about 99.2% (w/w), 50% (w/w) to about 95% (w/w), or of at least about 55% (w/w) to about 95% (w/w), or of at least about 60% (w/w) to about 95% (w/w), or of at least about 65% (w/w) to about 90% (w/w), or of at least about 70% (w/w) to about 85% (w/w), or of at least about 75% (w/w) to about 80% (w/w), or of at least 60% (w/w), or of at least about 65% (w/w), or of at least about 70% (w/w), or of at least about 75% (w/w), or of at least about 80% (w/w), or of at least about 85% (w/w), or of at least about 90% (w/w), or of at least about 95% (w/w).

In a particular preferred embodiment, the extraction solvent in the process according to the invention is ethanol in a concentration of about 92.6% (w/w), or water-free ethanol, e.g. absolute ethanol. Accordingly, the extraction solvent of step (a) of the process of the present invention may be ethanol in any of the concentrations as defined above, or the extraction solvent may be, e.g., absolute ethanol. Absolute ethanol may be obtained by any technique known in prior art, such as e.g. the use of molecular sieves, or e.g. synthetic zeolites, or cornmeal, or straw, or sawdust may be used to remove the residual water in the azetropic ethanol/water mixture, or, e.g., pressure-swing distillation may be used.

According to a preferred embodiment, the extraction solvent, the extraction solution and/or the concentrate does not comprise tetrahydrofuran. More preferably, the first organic solvent miscible with water and/or the second organic solvent miscible with water do not comprise tetrahydrofuran. Even more preferably, the inventive process is carried out without using tetrahydrofuran.

According to an even more preferred embodiment, the mass (weight) ratio of (dry) starting material, i.e. a resin of a plant of the genus *Boswellia*, to extraction solvent in the process according to the invention is at least about 1:5 (w/w) to about 1:20 (w/w), or at least about 1:6 (w/w) to about 1:15 (w/w), or at least about 1:8 (w/w) to about 1:12.5 (w/w), or at least about 1:10 (w/w) to about 1:20 (w/w), or at least about 1:6 (w/w), or at least about 1:7 (w/w), or at least about 1:8 (w/w), or at least about 1:9 (w/w), or at least about 1:8 (w/w), 1:9 (w/w), 1:10 (w/w), 1:11 (w/w), 1:12 (w/w), 1:13 (w/w), 1:14 (w/w), 1:15 (w/w), 1:16 (w/w), 1:17 (w/w), 1:18 (w/w), 1:19 (w/w), or 1:20 (w/w), preferably about 1:10 (w/w). Accordingly, for each mass unit of *Boswellia* resin used in the process according to the invention, the corresponding amount of extraction solvent as defined above is used, e.g. for a ratio of 1:5 (w/w) of *Boswellia* resin to extraction solvent, 100 g of *Boswellia* resin may be contacted with 500 g of extraction solvent, such as e.g. absolute ethanol.

In one embodiment, the extraction solvent comprises a supercritical fluid. The use of a supercritical fluid as an extraction solvent is well-known to the skilled person, who may select any suitable supercritical fluid and procedure accordingly. Preferably, the supercritical fluid is selected from the group comprising carbon dioxide, propane or butane. The supercritical fluid is preferably added to the resin by using any appropriate standard technique known in the art. Preferably, the supercritical fluid is used in combination with a first organic solvent miscible with water as defined herein.

Following step a), insoluble components are separated in step b) from the extraction solution obtained in the preceding step, wherein step b) preferably comprises a filtration or a centrifugation step. According to one embodiment, step b) comprises at least one filtration step, preferably as described herein. Such a filtration step may be selected from filtration techniques, such as, for the purposes of illustration only, microfiltration and/or ultrafiltration, respectively. Each filtration step may be conducted in one, two or more than two stages, if desired, combining the same of different filtration techniques. In this context, microfiltration is typically applied in order to remove material that would otherwise compromise the effectiveness of the ultrafiltration step.

Preferably, the separating step b) of the process according to the invention comprises filtration using a deep layer filtration, preferably a deep layer cellulose filter (e.g. AF15 or AF50 Filtrox). It is evident for the skilled person that any type of cellulose filter may be used in step b) of the process according to the invention, for as long as the filtration process removes and thereby separates insoluble material from the extraction solution.

In another embodiment, the separating step b) of the present invention comprises a step of centrifugation. Alternatively, any other separation method or combination of methods known in the art may be used for separating the insoluble components from the extraction solution.

After the separation of insoluble components from the extraction solution, said extraction solution is concentrated in step c) by evaporation and/or distillation. The evaporation step is preferably carried out at an elevated temperature of, e.g. from about 20° C. to 200° C., preferably of from about 20° C. to 100° C., preferably of from about 40° C. to 90° C., more preferably of from about 50° C. to 80° C., even more preferably of from about 40° C. to 70° C., such as of from about 55° C. to 65° C. The evaporation process may also be facilitated when carried out under reduced pressure of, e.g. 1 mbar to 500 mbar, preferably 10 mbar to 400 mbar, preferably 50 mbar to 350 mbar, more preferably from 100 mbar to 300 mbar. Preferably, the evaporation in step c) takes place at a reduced pressure from 5 to 300 mbar and at a temperature from 40° C. to 90° C., preferably from 50° C. to 80° C., more preferably from 55° C. to 65° C.

In addition to or alternatively to an evaporation step, a distillation step, preferably a steam distillation step, may also be included in step c) of the process according to the present invention. The distillation step preferably comprises heating of the extract solution to a temperature from 70° to 100° C., preferably to a temperature from 85° to 95° C. Preferably, the distillation step is carried out at a reduced pressure, e.g. at a pressure of preferably from 100 to 950 mbar, more preferably from 450 to 650 mbar. A water miscible solvent, preferably water, may optionally be added before distillation.

The duration of the evaporation or distillation step depends on the purpose of said step. If the volume of the extraction solution is to be reduced to a given volume (for instance, 15% of the initial volume or the volume before starting the evaporation/distillation step, respectively), evaporation or distillation is carried out until the desired volume is reached.

Preferably, the evaporation or distillation step is carried out for a certain time, which is required (based on the conditions) to free the extract solution of a volatile compound, preferably of undesired volatile compounds as defined herein, more preferably of a compound selected from the group consisting of limonene, linalool, thujone and estragol. The duration of the evaporation or the distillation step is preferably at least 5 minutes, 15 minutes, 20 minutes or 30 minutes, more preferably in the range from 10 minutes to 120 minutes, from 20 minutes to 90 minutes or from 30 minutes to 60 minutes. An evaporation step or a distillation step may comprise constant conditions (e.g. temperature, pressure) over the entire duration of said step or, alternatively, an evaporation or a distillation step may comprise variations, for instance, of temperature and/or pressure. More preferably, the evaporation or distillation step comprises at least two phases, which are characterized by different pressures. Therein, the pressure preferably decreases over time, e.g. the pressure is reduced in the second phase with respect to the pressure in the first phase. Preferably, the pressure in the first phase of the evaporation or distillation step is in the range from 600 to 950 mbar, while the pressure in the final phase of the evaporation or distillation step is in the range from 100 to 300 mbar. Most preferably, the temperature is reduced in the final phase as compared to the initial phase. The transition from the initial phase to the final phase may involve several intermediate steps comprising various pressures.

In a preferred embodiment, an additional purification step is carried out subsequently to step c) of the process, which comprises the following steps c1) and c2):

c1) purifying the extraction solution obtained in step c) from at least one protein interacting polyphenol by
  adding a second organic solvent miscible with water to the extraction solution, to reach a final concentration of 20-50% (w/w),
  adding a protein, preferably a protein solution or a protein suspension, or another compound interacting with a protein interacting polyphenol,
  optionally adding an inert granulate or powder, before, after or together with the addition of the protein, and
  precipitating protein-polyphenol-complexes by adjusting the concentration of the second organic solvent to 75-95% w/w;

c2) separating a precipitate obtained in step c1) by a process comprising at least one filtration step or at least one centrifugation step;

In step c1), the concentrated extract solution is preferably purified from at least one protein interacting polyphenol, preferably as defined herein. To this end, a second organic solvent miscible with water (or a mixture thereof with water) is added to the extraction solution in an amount to reach a final concentration of said second organic solvent miscible with water of preferably 10 to 70% (w/w) or 20 to 70% (w/w), more preferably 20 to 50% (w/w) or 30 to 70% (w/w). Most preferably, the second organic solvent miscible with water (or a mixture thereof with water) is added to the extraction solution in an amount to reach a final concentration of 20 to 50% (w/w).

The second organic solvent miscible with water is a solvent as defined herein with respect to the first organic solvent miscible with water. Preferably, the second organic solvent miscible with water comprises an alcohol, preferably selected from the group consisting of methanol, ethanol, isopropanol or an aromatic alcohol, more preferably ethanol or methanol, or a ketone, preferably acetone. The second organic solvent miscible with water according to the present invention is thus preferably selected, independently from the first organic solvent, from the group consisting of acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran and triethylene glycol. In a preferred embodiment of the process according to the present invention, the (first and/or second) solvent miscible with water is an alcohol, such as for example any of methanol, ethanol, isopropanol, aromatic alcohols, preferably ethanol or methanol, most preferably ethanol. Most preferably, a mixture of water and the second organic solvent miscible with water as defined herein, preferably a mixture of water and alcohol, more preferably a mixture of water and an alcohol selected from the group consisting of methanol, ethanol, isopropanol or an aromatic alcohol, more preferably ethanol or methanol, is added in step d) of the process. Most preferably, an ethanol/water mixture is added in step d) of the process. In one embodiment of the invention, the first and the second organic solvents miscible with water are identical. Alternatively, the first organic solvent miscible with water may be distinct from the second organic solvent miscible with water.

Step c1) of the process according to the invention further preferably comprises the addition to the extraction solution of a protein or of a synthetic polymer interacting with a protein interacting polyphenol.

According to a working hypothesis, the added protein or the added synthetic polymer interacts, preferably as described herein, with at least one compound selected from the group of polyphenols. Thus, a complex is preferably formed comprising the at least one compound selected from the group of polyphenols on the one hand and the added protein or synthetic polymer on the other hand. Preferably, the added protein molecules or the added synthetic polymer molecules are crosslinked by the at least one compound selected from the group of polyphenols. These protein-polyphenol-complexes or synthetic-polymer-polyphenol-complexes, respectively, are preferably less hydrophilic than the added protein or peptide. The protein or the synthetic polymer is preferably added at a final concentration of from 0.1 to 20% (w/w) or 0.5 to 20% (w/w), more preferably 1 to 10% (w/w), even more preferably 3 to 8% (w/w), most preferably to a final concentration of at least 2, 3 or 4% (w/w).

Step c1) of the process further comprises precipitating protein-polyphenol-complexes or polymer-polyphenol-complexes formed as described herein by adjusting the concentration of the second organic solvent miscible with water to a concentration of at least about 50% (w/w) to about 99.2% (w/w), 50% (w/w) to about 95% (w/w), or of at least about 55% (w/w) to about 95% (w/w), or of at least about 60% (w/w) to about 95% (w/w), or of at least about 65% (w/w) to about 90% (w/w), or of at least about 70% (w/w) to about 85% (w/w), or of at least about 75% (w/w) to about 80% (w/w), or of at least 60% (w/w), or of at least about 65% (w/w), or of at least about 70% (w/w), or of at least about 75% (w/w), or of at least about 80% (w/w), or of at least about 85% (w/w), or of at least about 90% (w/w), or of at least about 95% (w/w). Most preferably, the concentration of the second organic solvent miscible with water is adjusted to a concentration from 75% (w/w) to 95% (w/w).

In a preferred embodiment of the process according to the present invention, a protein or a protein solution is added to the extraction solution in step c1) of the process. Said protein or protein solution preferably comprises a protein or a peptide as defined herein, which interacts with a compound selected from the group of protein interacting polyphenols as defined herein.

The protein added in step c1) of the process according to the invention further comprises any compound having a peptide or protein moiety (characterized by the presence of at least two amino acids linked by a peptide bond), which is preferably capable of interacting with polyphenolic compounds, preferably with a compound selected from the group of polyphenols, preferably a protein interacting polyphenol, as defined herein.

In a preferred embodiment, a protein or a protein mixture of animal origin is added in step c1). Therein, a protein or a protein mixture derived from connective tissue is particularly preferred, such as collagen. A protein, which is added in step c1) of the process according to the invention is thus preferably a protein or a protein mixture derived from an animal tissue, which is characterized by a high collagen content. Preferably, a protein mixture of animal origin is used in step c1), e.g. isinglass, milk protein, casein or gelatin.

In a particularly preferred embodiment, gelatin is added in step c1) of the process according to the invention. As used herein, the term 'gelatin' refers to a mixture of compounds of animal origin, which is characterized by a high content of protein. Typically, gelatin is a mixture of animal proteins derived from collagen, preferably from irreversibly hydrolysed collagen. The gelatin is preferably added in step c1) as an aqueous gelatin solution or a suspension or a dispersion of gelatine in an aqueous solution. Preparations of gelatin are well-known in the art (e.g. Ph.Eur.) and may be employed in step c1) of the process according to the invention. Different types of gelatin may be used. Preferred gelatin types comprise gelatin derived from mammalian (preferably bovine or pork), avian (preferably chicken) or fish origin. The term 'gelatin' as used herein also comprises gelatin, which was obtained by any known procedure, such as specific hydrolization procedures, without being limited to a certain type or grade. In the context of the invention, any commercially available gelatin may be used, irrespective of its origin and specific (e.g. physical) properties. Preferably, food or pharmaceutical grade gelatin is used. Notably, the use of a protein as described herein, is distinct from its use in the prior art, in particular in the food industry. Before the present invention, it has never been suggested to employ a protein, in particular a gelatin or a solution, suspension or dispersion thereof, in the context of lipophilic extracts.

In a preferred embodiment, a gelatin is added in step c1) of the process according to the present invention in an amount sufficient for reaching a final concentration of 0.1 to 20 (w/w) or 0.5 to 20% (w/w), more preferably 1 to 10% (w/w), even more preferably 3 to 8% (w/w), most preferably to a final concentration of at least 2, 3 or 4% (w/w).

Alternatively, proteins of plant origin, such as proteins derived from fruits, vegetables or any other part of a plant, may be used. Preferably, the protein, which is added in step c1) of the process according to the present invention, is derived from a plant of the family Leguminosae, more preferably derived from peas, chickpeas, beans or lentils. Further, mixtures of several types of plant proteins may be employed, such as a mixture of proteins from different plants.

In a preferred embodiment, a mixture of a protein of animal origin and a protein of plant origin is used in step c1). Preferably, a protein or protein mixture of animal origin having a high collagen content is used in combination with a plant protein derived from a plant of the family Leguminosae. More preferably, a gelatin and a protein derived from a plant from the family Leguminosae is used.

In a further preferred embodiment of the process according to the present invention, a synthetic polymer interacting with a protein interacting polyphenol or a solution of said polymer is added to the extraction solution in step c1) of the process.

In the context of the present invention, the phrase 'synthetic polymer interacting with a protein interacting polyphenol' (or the phrase 'synthetic polymer' used in this context) comprises any synthetic polymer compound, which interacts with a protein interacting polyphenol as defined herein. The interaction between the synthetic polymer and the protein interacting polyphenol is typically analogous to the interaction of the polyphenol with the protein as described herein. The phrase further comprises any synthetic polymer, irrespective of its structure, which is capable of interacting with a protein interacting polyphenol. The interaction of a synthetic polymer with a protein interacting polyphenol is readily determined by the skilled person, e.g. by addition of the synthetic polymer to a solution having a known concentration of a protein interacting polyphenol and quantification of the amount of protein interacting polyphenol in the supernatant after centrifugation. In the context of the present invention the phrase 'synthetic polymer' comprises any chemically synthesized polymer (such as, for instance, nylon, polyvinyl, polyamide polystyrene, polyethylene, polypropylene, polyacrylonitrile, synthetic rubber, phenol formaldehyde resin (or Bakelite), neoprene, silicone and derivatives of each of these). Furthermore, the phrase 'synthetic polymer' comprises any polymeric compound of natural origin, which has been modified chemically (such as, for instance, nitrocellulose). The term 'polymer' as used in this context typically refers to a macromolecule comprising repetitive units (monomers). The repetitive units may be identical (homopolymer) or distinct from each other (copolymer). Depending on its structure, a polymer in the meaning of the present invention may be a linear or a branched polymer. In particular, a polymer in the meaning of the present invention may be a so-called 'popcorn polymer', which is characterized by its popcorn or cauliflower-like appearance. Furthermore, the polymer may be a block polymer or a block copolymer and comprise distinct blocks comprising repetitive units (so-called 'blocks', which represent polymer subunit of the block polymer of block copolymer), wherein the polymer comprises one type of blocks (block polymer) or at least two distinct types of blocks (block copolymer).

Preferably, a synthetic polymer as defined herein is added in step c1) of the process according to the invention, wherein the polymer is insoluble in any solvent. More preferably, the polymer is insoluble in water. In a further preferred embodiment, the synthetic polymer has a favourable safety and tolerability profile, rendering it suitable for the use of the extract as, e.g., a medicament, a food or in a cosmetic composition.

In a preferred embodiment, step c1) comprises the addition of a popcorn polymer interacting with a protein interacting polyphenol. A 'popcorn polymer', as used herein, is typically a crosslinked polymer or copolymer, which is preferably insoluble in water, more preferably insoluble in alcohol, preferably ethanol, or even more preferably insoluble in any solvent. More specifically, the term 'popcorn polymer' as used herein refers to an insoluble crosslinked polymer or copolymer as defined herein, wherein the polymer or copolymer is preferably a polyvinyl polymer. Further, the term comprises insoluble polyvinyl block polymers or block copolymers (e.g. PVP block polymers or block copolymers, comprising, for instance, a monomer derived from vinyl acetate). In the context of the present invention, a polyvinyl polymer typically comprises a monomer of the general formula [—CH2-CHR—], wherein R is not hydrogen. Therein, R is preferably 2-pyrrolidone.

Preferably, the synthetic polymer added in step c1) is a crosslinked form of poly(vinylpyrrolidone) (also known as Divergan, PVP, polyvidone or povidone). Most preferably, crospovidone (also referred to as polyvinylpolypyrrolidone, PVPP, crosolividone or E1202) or a related compound is used.

Alternatively, the synthetic polymer added in step c1) may be a polyamide, preferably a polyamide powder.

Preferably, a synthetic polymer interacting with a protein interacting polyphenol is added at a final concentration in the range from 0.1% (w/w) to 5% (w/w), more preferably from 0.5% (w/w) to 2% (w/w).

In a particularly preferred embodiment of the process according to the invention, step c1) comprises the addition of a crosslinked form of poly(vinylpyrrolidone), preferably crospovidone, at a final concentration in the range from 0.1% (w/w) to 5% (w/w), more preferably from 0.5% (w/w) to 2% (w/w).

In another embodiment, step c1) comprises the addition of both, a protein as defined herein as well as a synthetic polymer interacting with a protein interacting polyphenol as described herein.

In order to increase the efficiency of the precipitation in step c1), an inert granulate or powder, preferably a cellulose powder, is preferably added before, after or concurrently with the addition of the protein or the synthetic polymer. According to a working hypothesis, addition of an inert granulate or powder leads to formation of a dispersion, wherein the particles derived from the inert granulate or powder act as an adsorbant for protein-polyphenol-complexes or polymer-polyphenol-complexes, respectively. The complexes formed in step c1) preferably interact with the particles of the inert granulate or powder and, upon increase of the concentration of the second organic solvent miscible with water, precipitate. The inert granulate or powder is thus also referred to as 'flocking agent'.

Preferably, an inert granulate or powder is derived from a compound comprising fibers, preferably from an organic compound, preferably a dispersible organic compound, comprising or consisting of fibers, more preferably from an organic biomolecule having a fibrous structure, even more preferably a carbohydrate. Preferably, the inert granulate or powder is insoluble and forms dispersions, preferably without swelling. The inert granulate or powder is preferably characterized by a mean particle size in the range from 0.01 to 10 mm. More preferably, a cellulose powder is used as inert material in step d). Alternatively, other powders derived from fibrous organic material (e.g. inulin) is preferably employed as inert granulate or powder.

In another preferred embodiment of the present invention, step a) of the process comprises the addition of a synthetic polymer interacting with a protein interacting polyphenol (as defined herein with respect to step c1)). Preferably, a crosslinked form of poly(vinylpyrrolidone), preferably crospovidone, is added in step a) at a concentration in the range from 0.1% (w/w) to 5% (w/w), more preferably from 0.5% (w/w) to 2% (w/w). More preferably, step a) comprises the addition of crospovidone or a related compound and further the addition of an inert granulate powder, preferably as defined herein. Therein, the inert granulate or powder is preferably added at a concentration in the range from 0.1% (w/w) to 10% (w/w), more preferably from 0.5% (w/w) to 4% (w/w). Therein, a cellulose powder is preferably used as inert material. Without being bound to any theory, it is believed that the addition of a crosslinked form of poly(vinylpyrrolidone), preferably crospovidone, and further (optionally) the addition of an inert granulate or powder, preferably a cellulose powder, reduces the concentration of a compound selected from protein interacting polyphenols in the extract.

Subsequently to step c1), the precipitate obtained in step c1) is separated from the extraction solution in step c2) by a process comprising at least one filtration step or at least one centrifugation step, preferably as defined herein with respect to step b) of the process according to the invention.

In a preferred embodiment, step c2) comprises at least two filtration steps, wherein a diatomaceous earth is added to the obtained first filtrate, wherein the diatomaceous earth preferably interacts with the formed protein-polyphenol- or synthetic-polymer-polyphenol-complexes and/or with non-complexed protein or polymer. In the context of the present invention, the term 'diatomaceous earth' refers to a naturally occurring siliceous mineral, typically provided in the form of a powder. The diatomaceous earth preferably has a particle size ranging from less than 1 μm to 1 mm, more preferably from 10 to 200 μm. Preferred diatomaceous earths comprise, but are not limited to, Sanacel, Celite, Perlit, bentonite, Bentonit, silica sand, a silicate or a sol of silicic acid. Preferably, the diatomaceous earth added in step c1) interacts with protein or with a synthetic polymer that is not complexed by a compound selected from the group of protein interacting polyphenols (e.g. excess protein, such as gelatin). The non-complexed protein or polymer is then retained by the filter together with the diatomaceous earth. That procedure is preferably used in order to purify the extract solution from protein or synthetic polymer, preferably from protein, that has been added in step c1), which has not been precipitated in step c1).

Following step c), or, if optional steps c1) and c2) were carried out, following step c2), a lipid phase is optionally added to the extraction solution in step d). Therein, the lipid phase is preferably added to the extraction solution in the form of a lipid solution, in a waxy form, in the form of an oily liquid or in the form of an oily semi-solid. Preferably, the lipid phase added in step d) comprises a mono-, di- or triglyceride, i.e. a compound derived from esterification of a glycerol with one, two or three medium or long chain fatty acids, respectively; a linear hydrocarbon with a melting point of at least 10° Celsisus; polyglycerin fatty acid esters, propylene glycol fatty acid esters, polyethyleneglycol polymers and functionalized polymers; an emulsifier (polysorbates, PEG-40 hydrogenated castor oil, polyglycerol-polyricinoleate); or co-solvents, such as glycerol, propylene glycol or ethyleneglycol monoethylether.

In a preferred embodiment, middle-chain monoglycerides, middle-chain diglycerides or middle-chain triglycerides are added to the extract solution. As used herein, a 'middle-chain glyceride' (or medium-chain glyceride) refers to mono-, di- or triglycerides, wherein glycerol has been esterified with one, two or three fatty acids, respectively, wherein the fatty acids preferably comprise 6 to 12 carbon atoms. Preferably, middle-chain diglycerides and middle-chain triglycerides are added in step f) of the process, either independently or as a mixture. More preferably, middle-chain monoglycerides, middle-chain diglycerides and middle-chain triglycerides are added, either independently or as a mixture. The added lipid is preferably Labrafac, Peceol, a combination of Labrafac and Peceol, or a comparable commercially available lipid or lipid mixture with comparable chemical and physical properties.

Preferably, a lipid or a mixture of lipids as defined herein is added to a final lipid concentration of at least 0.01% (w/w), at least 0.05% (w/w), at least 0.1% (w/w), at least 1% (w/w), at least 2% (w/w), at least 3% (w/) or to a final concentration in a range from 0.01 to 15% (w/w), preferably from 0.1 to 10% (w/w), more preferably from 0.5 to 5% (w/w). Preferably, the lipid phase optionally added in step d) further increases the content of the extract of a compound selected from the group of triterpenic acids and derivatives thereof and/or the content of a compound selected from the group of cyclic diterpenoids or derivatives thereof, preferably a monocyclic diterpenoid, more preferably a monocyclic diterpenic alcohol or a derivative thereof, even more preferably a compound from the group of cembranoids, as defined herein, and derivatives thereof. A compound selected from the group of triterpenic acids or derivatives thereof and/or a compound selected from the group of cyclic diterpenoids or derivatives thereof, preferably a monocyclic diterpenoid, more preferably a monocyclic diterpenic alcohol or a derivative thereof, even more preferably a compound from the group of cembranoids, as defined herein, and derivatives thereof, preferably dissolves in the lipid phase optionally added in step d), which preferably prevents loss of the compound selected from the group of triterpenic acids or derivatives thereof and/or a compound selected from the group of diterpenic alcohols or derivatives thereof during subsequent evaporation and/or distillation step(s), thus retaining said compounds in the extract solution.

In subsequent step e) of the process according to the invention, the extraction solution is concentrated by distillation, preferably steam distillation, and/or evaporation. Preferably, the concentration comprises an evaporation step and/or a distillation step as described herein with respect to step c). More preferably, the extraction solution is concentrated by an evaporation step, which comprises heating of the extraction solution to a temperature from 40° to 90° C., preferably from 50° to 80°, more preferably from 55° to 65° C., preferably at a reduced pressure from 100 to 300 mbar, preferably for at least 5 minutes, 15 minutes, 20 minutes or 30 minutes, more preferably for a duration in the range from 10 minutes to 120 minutes, from 20 minutes to 90 minutes or from 30 minutes to 60 minutes.

In step f) according to the present invention, a suitable amount of water is added to the concentrated extraction solution obtained in step e) and the resulting mixture is subjected to a distillation step, preferably as defined herein with respect to step c). The distillation step preferably comprises heating of the extract solution to a temperature from 70° to 100° C., preferably to a temperature from 85° to 95° C. Preferably, the distillation step is carried out at a reduced pressure, e.g. at a pressure of preferably from 100 to 950 mbar, more preferably from 450 to 650 mbar. The duration of the distillation step is preferably at least 5 minutes, 15 minutes, 20 minutes or 30 minutes, more preferably in the range from 10 minutes to 120 minutes, from 20 minutes to 90 minutes or from 30 minutes to 60 minutes. A distillation step may comprise constant conditions (e.g. temperature, pressure) over the entire duration of said step or, alternatively, a distillation step may comprise variations, for instance, of temperature and/or pressure. More preferably, the distillation step comprises at least two phases, which are characterized by different pressures. Therein, the pressure preferably decreases over time, e.g. the pressure is reduced in the second phase with respect to the pressure in the first phase. Preferably, the pressure in the first phase of the distillation step is in the range from 600 to 950 mbar, while the pressure in the final phase of the evaporation or distillation step is in the range from 100 to 300 mbar. The transition from the initial phase to the final phase may involve several intermediate steps comprising various pressures. For example, the distillation step in step f) may be carried out at 90° C., 900 mbar for 30 minutes (first phase), 90° C., 600 mbar for 30 minutes (second phase), and 90° C., 200 mbar for 20 minutes (third phase).

Following distillation, the extraction solution is further subjected to evaporation in step f). The evaporation step is preferably carried out as described herein with respect to step c). Preferably, the evaporation step is carried out at an elevated temperature of, e.g. from about 20° C. to 200° C., preferably of from about 20° C. to 100° C., preferably of from about 40° C. to 90° C., more preferably of from about 50° C. to 80° C., even more preferably of from about 40° C.

to 70° C., such as of from about 55° C. to 65° C. The evaporation process may also be facilitated when carried out under reduced pressure of, e.g. 1 mbar to 500 mbar, preferably 10 mbar to 400 mbar, preferably 50 mbar to 350 mbar, more preferably from 100 mbar to 300 mbar. Preferably, the evaporation in step c) takes place at a reduced pressure from 100 to 300 mbar and at a temperature from 40° C. to 90° C., preferably from 50° C. to 80° C., more preferably from 55° C. to 65° C. Most preferably, the evaporation step in step f) is carried out at a temperature in the range from 55° C. to 65° C. and at a pressure in the range from 1 to 200 mbar.

After complete evaporation of the solvent(s) in step f), the purified extract, preferably a solvent-free extract, is obtained. In one embodiment of the invention, said extract is a dry extract, preferably a dry powder.

Alternatively, if a lipid phase was added in step d) (or if not all of the water/solvent was evaporated), a liquid or semi-solid purified extract, preferably as defined herein, is obtained. Preferably, the liquid or semi-solid extract is an oily extract, which preferably consists of a single lipid phase. Most preferably, the single lipid phase comprises a compound selected from the group of triterpenic acids or derivatives thereof and preferably further comprises a compound selected from the group of cyclic diterpenoids or derivatives thereof, preferably a monocyclic diterpenoid, more preferably a monocyclic diterpenic alcohol or a derivative thereof, even more preferably a compound from the group of cembranoids, as defined herein, and derivatives thereof.

The pH value of the extraction solvent, the extraction solution and/or the concentrate is preferably in a range from 3 to 10, more preferably in a range from about 3.5 to about 8, even more preferably in a range from about 4 to about 7. According to a preferred embodiment, the pH value of the extraction solvent, the extraction solution and/or the concentrate is about 7 or less. More preferably, the pH value of the extraction solvent, the extraction solution and/or the concentrate is in a range from about 5 to about 6. In a preferred embodiment, all steps of the inventive process take place in a medium having a pH of about 7 or below.

In a particularly preferred embodiment of the present invention, the process for preparing an extract from the resin of a plant of the genus *Boswellia*, wherein the amount in the extract of at least one compound selected from the group consisting of limonene, linalool, thujone and estragol, and/or the amount of at least one compound selected from the group of protein interacting polyphenols, is reduced in comparison to a conventional extract of the same resin, comprises the steps of:

a) contacting the resin with an extraction solvent to obtain an extraction solution, wherein the extraction solvent comprises ethanol or an ethanol-water mixture; optionally adding a crosslinked poly(vinylpyrrolidone) compound and an inert granulate or powder, preferably a cellulose powder, b) separating insoluble components from said extraction solution by a technique comprising a filtration or centrifugation step, c) concentrating said extraction solution by evaporation and/or distillation, preferably steam distillation, c1) purifying said extraction solution from at least one protein interacting polyphenol by adding ethanol to the extraction solution, to reach a final concentration of 20-50% (w/w),
  adding a protein, preferably a gelatin solution or a gelatin suspension,
  optionally adding an inert granulate or powder, preferably cellulose powder, before, after or together with, preferably together with, the addition of the protein, and precipitating protein-polyphenol-complexes by adjusting the ethanol concentration to 75-95% w/w;

c2) separating a precipitate obtained in step c1) by a process comprising at least two filtration steps, wherein diatomaceous earth is added to the first filtrate;

d) adding a lipid phase as defined herein, e) concentrating the obtained extraction solution by distillation, preferably steam distillation, and/or evaporation;

f) purification of the obtained concentrate by adding water and distillation, followed by evaporation and finally obtaining a liquid or semi-solid extract as defined herein.

In a preferred aspect of the present invention, the purified extract obtained in step f) is characterized by the features defined herein with respect to the extract according to the present invention. It is further encompassed that the extract obtained in step f) of the process according to the invention is further processed, e.g. by further purification steps.

In another aspect, the present invention provides an extract from a resin of a plant of the genus *Boswellia*, which is obtainable by the process as described herein.

In a preferred embodiment, the extract obtained by the process according to the invention as described above is an extract, which is characterized by the features as described above with respect to the extract according to the invention.

In a particularly preferred embodiment, the purified extract, which is obtainable by the process according to the present invention has a content of each of limonene, linalool, thujone of less than 20 ppm, preferably less than 10 ppm, and a content of estragol of less than 100 ppm, wherein the content is calculated based on the dry weight of the extract. Preferably, the extract, which is obtainable by the process has a content of linalool of less than 20 ppm, a content of each of limonene and thujone of less than 10 ppm and a content of estragol of less than 100 ppm. More preferably, said extract is further characterized in that the content of at least one compound selected from the group of protein interacting polyphenols, is reduced in comparison to a conventional extract of the resin.

Preferably, the purified extract, which is obtainable by the process according to the present invention comprises a compound selected from the group of triterpenic acids or derivatives thereof as defined herein. More preferably, the extract comprises a compound selected from the group of cyclic, preferably monocyclic, diterpenoids or derivatives thereof as defined herein. Most preferably, the extract, which is obtainable by the inventive process is further characterized by the specific contents and weight ratios of said compounds as defined herein with respect to the extract according to the invention.

In another aspect, the present invention provides a composition comprising the inventive extract from the resin of a plant of the genus *Boswellia* as defined above or the extract obtainable by the inventive process a defined above.

In a preferred embodiment, the composition comprising the inventive extract is a pharmaceutical composition, which further comprises at least one additional pharmaceutically acceptable excipient. Preferably, the pharmaceutical composition comprises the inventive *Boswellia* extract as an active ingredient and further comprises at least one other excipient, which is suitable for pharmaceutical use in a subject. In the context of the present invention, the term 'subject' preferably relates to a 'patient', an 'individual', or an 'animal', which terms preferably relate to a mammal. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term 'animal' as used herein also includes humans. A preferred 'subject' in the context of the present invention is a human.

The term 'excipient' when used herein is intended to indicate all substances in a pharmaceutical formulation or pharmaceutical composition, which are not pharmaceutically active ingredients such as, e.g. carriers, binders, lubricants, thickeners, disintegrants, surface active agents, preservatives, emulsifiers, buffers, flavouring agents, colorants, glidants, coatings or protective matrices etc. The term 'pharmaceutically acceptable' refers to those properties and/or substances, which are acceptable to the patient from a pharmacological/toxicological point of view and to the manufacturing pharmaceutical chemist from a physical/chemical point of view regarding factors such as formulation, stability, patient acceptance and bioavailability.

The pharmaceutical composition according to the present invention may be prepared in any suitable manner known to the person skilled in the art, e.g. depending on the intended administration route. Preferably, the composition is prepared using known techniques and excipients, which are compatible with the lipophilic nature of the components of the inventive *Boswellia* extract.

The liquid forms of the pharmaceutical compositions according to the present invention, e.g. for oral administration or administration by injection, include, for example, aqueous solutions or suspensions, liposomal preparations, micro- or nano-emulsions, alcoholic solutions, optionally flavoured syrups, aqueous, alcoholic or oil suspensions, and optionally flavoured emulsions with edible oils such as cottonseed oil, sesame oil, coconut oil or peanut oil etc.

For preparing solid compositions such as tablets, the pharmaceutically active ingredient(s) is/are mixed with a pharmaceutical excipient or carrier, e.g. conventional tableting ingredients such as corn starch, lactose, sucrose, sorbitol, talc, stearic acid, magnesium stearate, dicalcium phosphate or gums, and optionally pharmaceutical diluents to form a solid preformulation composition containing a homogenous mixture of the compound according to the present invention. The solid pre-formulation composition may then be subdivided into unit dosage forms. Tablets or pills may be coated or otherwise compounded to provide a dosage form affording the advantage of, e.g. prolonged action or improved delivery.

The pharmaceutical composition is typically provided in the form of a dosage form suitable for administration of the inventive *Boswellia* extract, preferably via oral administration, via parenteral administration, preferably via injection, via rectal administration, via vaginal administration, or via topical administration.

Particularly preferred dosage forms of the pharmaceutical composition according to the invention comprise, but are not limited to, the group consisting of a capsule, preferably a soft gelatin capsule or a hard capsule; a troche; a lozenge; an aqueous or oily solution or suspension; a dispersible powder or granulate, preferably a melt extrusion granulate; an emulsion; a syrup; a tablet, preferably a sustained-release or an immediate-release tablet; a suppository; a dermal patch, an ointment; a gel; a cream; a spray; or a lotion.

In a preferred embodiment, the pharmaceutical composition according to the present invention is prepared as an oral dosage form suitable for oral administration, for example, as capsules, tablets, troches, lozenges, aqueous or oily suspensions or solutions, dispersible powders or granules, emulsions, hard or soft capsules, or syrups or elixirs. Such compositions may contain one or more agents selected from the group consisting of sweetening agents, flavouring agents, colouring agents and preserving agents in order to provide pharmaceutically elegant and palatable preparations. In the case of tablets for oral use, carriers commonly used include lactose and corn starch. Lubricating agents, such as magnesium stearate, are also typically added. For oral administration in a capsule form, useful diluents include lactose and dried corn starch. When aqueous suspensions are required for oral use, the inventive extract as defined herein, may be combined with emulsifying and suspending agents. If desired, certain sweetening, flavouring or colouring agents may also be added. Tablets typically contain the dry extract according to the invention in admixture with non-toxic pharmaceutically acceptable excipients such as, for example, inert diluents such as calcium carbonate, sodium carbonate, lactose, calcium phosphate or sodium phosphate; granulating and disintegrating agents, for example corn starch or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated, to form osmotic therapeutic tablets for controlled release. Formulations for oral use may also be presented as hard gelatin capsules wherein the active ingredient(s) is mixed with an inert solid diluent, for example calcium carbonate, calcium phosphate or kaolin.

In a particularly preferred embodiment, the pharmaceutical composition is provided as soft gelatin capsules or as soft vegetable capsules, wherein the active ingredient is mixed with water or an oil medium (for example peanut oil, liquid paraffin or olive oil) or lecithine or fractions of lecithine (e.g. Phospholipon 90 G®) or other suitable emulsifying agents. Advantageously, the reduced concentration of protein interacting polyphenols as defined herein prolongs the stability of a gelatin capsule, preferably a soft gelatin capsule, comprising the inventive extract. When conventional *Boswellia* extracts are used, which have a considerable amount of protein interacting polyphenols, said polyphenols interact with the gelatin in the capsules, which leads to decreased stability and reduced shelf life. By using the inventive extract, the interaction with the gelatin in the capsule is reduced due to the reduced concentration of protein interacting polyphenols in the extract. Therefore, stability and/or shelf life of a gelatine capsule, preferably a soft gelatine capsule, is increased when the inventive extract is used.

In another preferred embodiment, the pharmaceutical composition according to the invention is provided in the form of suppositories for rectal administration of the composition. Such compositions can be prepared by mixing the composition as defined above with a suitable non-irritating excipient which is solid at ordinary temperatures but liquid at the rectal temperature and will therefore melt in the rectum to release the drug. Such materials are cocoa butter and polyethylene glycols.

Aqueous suspensions in the above context, preferably for oral administrations, for administrations via the gastrointestinal tract comprising the inventive pharmaceutical compositions, may contain the inventive composition as defined above in admixture with suitable excipients. Such excipients are suspending agents, for example sodium carboxymethylcellulose, methylcellulose, hydroxypropylmethyl-cellulose, sodium alginate, polyvinyl pyrrolidone, gum tragacanth and gum acacia; dispersing or wetting agents, for example a naturally occurring phosphatide such as lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, such as a polyoxyethylene with partial esters derived from fatty acids and hexitol anhydrides, for example polyoxyethylene sorbitan monooleate. Aqueous suspensions may also contain one or more preservatives, for example ethyl or n-propyl p-hydroxybenzoate, one or more colouring agents, one or more flavouring agents, and one or more sweetening agents, such as sucrose or saccharin.

In a preferred embodiment, the pharmaceutical composition is provided as a transdermal therapeutic system, for instance as a dermal patch, an ointment; a gel; a cream; a spray or a lotion.

A dosage unit of the pharmaceutical composition according to the invention preferably comprises a safe and effective amount of the inventive extract. As used herein, a 'safe and effective amount' means an amount of the active ingredient as defined herein as such that is sufficient to significantly induce a positive modification of a disease as defined herein. At the same time, however, a 'safe and effective amount' is small enough to avoid serious side-effects and to permit a sensible relationship between advantage and risk. The determination of these limits typically lies within the scope of sensible medical judgment. A 'safe and effective amount' of the active ingredient(s) of the inventive pharmaceutical composition, particularly of the composition as defined herein, will furthermore vary in connection with the particular condition to be treated and also with the age and physical condition of the patient to be treated, the body weight, general health, sex, diet, time of administration, rate of excretion, drug combination, the activity of the extract as defined herein, the severity of the condition, the duration of the treatment, the nature of the accompanying therapy, of the particular pharmaceutically acceptable carrier used, and similar factors, within the knowledge and experience of the accompanying physician. The dose to be administered may thus depend on the individual to be treated, e.g. mice may require a higher dosing per kg body weight of the inventive pharmaceutical composition than humans, or vice versa.

Most preferably, the composition is provided in a dosage unit, which comprises from 50 to 5000 mg of the extract, preferably from 200 to 3500 mg, more preferably from 300 to 2500 mg, even more preferably from 400 to 2000 mg, or most preferably from 250 to 1500 mg.

According to a more preferred embodiment, a dosage unit of the pharmaceutical composition as defined above may be administered at least once a day, or e.g. one to four times daily, e.g. once, twice, three times or four times a day, preferably three times a day. Thus, the inventive pharmaceutical composition as defined above may be administered, e.g. once, twice, three times or four times per day. The administration may be e.g. prior to, or concurrent with, or following food intake of the patient. The best time for administration is to be determined on a case-to-case basis by the accompanying physician.

In a preferred embodiment, the pharmaceutical composition according to the invention comprises as a first active ingredient the inventive *Boswellia* extract as defined herein and further a second active ingredient. Preferably, the second active ingredient is a compound, which is known to be effective in the treatment or prophylaxis of a disease as defined herein.

In another aspect, the pharmaceutical composition according to the present invention is provided for use as a medicament. Furthermore, the present invention concerns the use of the extract as defined herein in the manufacture of a medicament. Therein, the medicament is preferably characterized by the features defined herein with respect to the pharmaceutical composition according to the present invention.

In a preferred embodiment, the pharmaceutical composition as defined herein or the medicament comprising the extract as defined herein is provided for use in the treatment and/or prevention of a disease, wherein the disease is preferably selected from the group consisting of a neurodegenerative disease, an inflammatory disease, an autoimmune disease, a tumour disease and an infectious disease.

The term 'neurodegenerative diseases' as used herein comprises, but is not limited to, Alzheimer's disease, Parkinson's disease, Huntington's disease, multiple sclerosis, amyotrophic lateral sclerosis, Lewy body dementia, vascular dementia, prion diseases, motor neurone diseases (MND), spinocerebellar ataxia (SCA) or spinal muscular atrophy (SMA).

The term 'inflammatory diseases' as used herein typically refers to a disorder, which involves an abnormal inflammation reaction. For example, the term comprises, without being limited thereto, atherosclerosis, ischaemic heart disease, acne vulgaris, asthma, autoinflammatory diseases, celiac disease, chronic prostatitis, glomerulonephritis, hypersensitivities, inflammatory bowel disease, pelvic inflammatory disease, reperfusion injury, rheumatoid arthritis, sarcoidosis, transplant rejection, vasculitis or interstitial cystitis.

'Autoimmune diseases' as used herein, may be divided into the categories of systemic syndromes, including systemic lupus erythematosus (SLE), Sjögren's syndrome, scleroderma, rheumatoid arthritis and polymyositis or local syndromes, which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (diabetes mellitus type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, polymyalgia rheumatica, progressive systemic sclerosis (PSS), Reiter's syndrome, rheumatic arthritis, psoriasis, vasculitis, lichen planus, etc, or type II diabetes.

In the context of the present invention, a cancer or a tumour disease preferably includes e.g. solid tumours of neurogenic, mesenchymal or epithelial origin and metastases thereof, colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours, mammary carcinomas, prostate tumours, hepatomas, various virus-induced tumours such as, for example, papilloma virus-induced carcinomas (e.g. cervical carcinoma), adenocarcinomas, herpes virus-induced tumours (e.g. Burkitt's lymphoma, EBV-induced B-cell lymphoma), heptatitis B-induced tumours (hepatocell carcinoma), HTLV-1- and HTLV-2-induced lymphomas, acoustic neuromas/neurinomas, cervical cancer, lung cancer, pharyngeal cancer, anal carcinomas, glioblastomas, lymphomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, osteosarcomas, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour, prostate cancer, etc., particularly solid tumours of neurogenic, mesenchymal or epithelial origin and metastases thereof.

'Infectious diseases' are caused by pathogenic microorganisms, such as bacteria, viruses, parasites or fungi. Examples of infectious diseases comprise influenza, malaria, SARS, yellow fever, AIDS, Lyme borreliosis, Leishmaniasis, anthrax, meningitis, viral infectious diseases such as AIDS, condyloma *acuminata*, hollow warts, dengue fever, three-day fever, ebola virus, cold, early summer meningoencephalitis (FSME), flu, shingles, hepatitis, Herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), from bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella* paratyphus, *Salmonella* typhus, scarlet fever, syphilis, tetanus, tripper, tsutsugamushi disease, tuberculosis, typhus, vaginitis (colpitis), soft chancre, and from infectious diseases caused by parasites, protozoa or fungi, such as amoebiasis, bilharziosis, Chagas disease, athlete's foot, yeast fungus spots, scabies, malaria, onchocercosis (river blindness), or fungal diseases, toxoplasmosis, trichomoniasis, trypanosomiasis (sleeping sickness), visceral Leishmaniosis, nappy/diaper dermatitis, schistosomiasis, fish poisoning (Ciguatera), candidosis, cutaneous Leishmaniosis, lambliasis (giardiasis), or sleeping sickness, or from infectious diseases caused by *Echinococcus*, fish tapeworm, fox tapeworm, canine tapeworm, lice, bovine tapeworm, porcine tapeworm or miniature tapeworm In a particularly preferred embodiment, the pharmaceutical composition as defined herein or the medicament comprising the extract as defined herein is provided for treatment and/or prevention of a disease is selected from the group consisting of multiple sclerosis, amyotrophic lateral sclerosis, morbus Crohn, psoriasis, atopic dermatitis, glioblastoma, peritumoral edema, rheumatic diseases, respiratory diseases and lupus erythematodes.

Preferably, the pharmaceutical composition as defined herein or the medicament comprising the extract as defined herein administered prior and/or concurrent with and/or subsequent to a conventional treatment of the respective disease, preferably a disease as defined herein.

The pharmaceutical composition as defined herein or the medicament comprising the extract as defined herein is preferably administered via the respiratory tract, via oral administration or may be administered by injection, typically via parenteral injection, preferably by subcutaneous, intravenous, intramuscular, intra-articular, intra-synovial, intrasternal, intrathecal, intrahepatic, intralesional, intracranial, transdermal, e.g. via transdermal therapeutic delivery systems such as dermal patches, intradermal, intrapulmonal, intraperitoneal, intracardial, intraarterial, and sublingual injection or via infusion techniques. More preferably, administration of the inventive pharmaceutical composition occurs by intravenous or, more preferably, intramuscular injection, yet most preferably by an inhalator as an aerosol or micro/nano-emulsion via the respiratory tract or via oral administration. The composition might also be administered vaginally or via the gastrointestinal system, e.g. rectally, e.g. via suppositories.

Most preferably, the pharmaceutical composition as defined herein or the medicament comprising the extract as defined herein is administered via oral administration, via parenteral administration, preferably via injection, via rectal administration, via vaginal administration, or via topical administration.

Preferably, the pharmaceutical composition as defined herein or the medicament comprising the extract as defined herein is administered at least once a day or one to four times a day, preferably once, twice, three times or four times a day.

According to a preferred embodiment, the inventive pharmaceutical composition as defined above or the medicament comprising the extract as defined herein may be administered at a dose of at least about 10 mg/kg body weight to about 200 mg/kg body weight, or of at least 10 mg/kg body weight to about 200 mg/kg body weight, or of at least 12.5 mg/kg body weight to about 190 mg/kg body weight, or of at least about 15 mg/kg body weight to about 190 mg/kg body weight, or of at least about 20 mg/kg body weight to about 180 mg/kg body weight, or of at least about 25 mg/kg body weight to about 170 mg/kg body weight, or of at least about 30 mg/kg body weight to about 160 mg/kg body weight, or of at least about 35 mg/kg body weight to about 160 mg/kg body weight, or of at least about 40 mg/kg body weight to about 150 mg/kg body weight, or of at least about 45 mg/kg body weight to about 140 mg/kg body weight, or of at least about 50 mg/kg body weight to about 130 mg/kg body weight, or of at least about 55 mg/kg body weight to about 120 mg/kg body weight, or of at least about 60 mg/kg body weight to about 110 mg/kg body weight, or of at least about 65 mg/kg body weight to about 100 mg/kg body weight, or of at least about 70 mg/kg body weight to about 90 mg/kg body weight, or of at least about 75 mg/kg body weight to about 85 mg/kg body weight, preferably of about 10-200 mg/kg body weight, or of about 25 to about 190 mg/kg body weight, or of about 30 mg/kg body weight to about 180 mg/kg body weight, or of about 10 mg/kg body weight, or of about 12.5 mg/kg body weight, or of about 15 mg/kg body weight, or of about 17.5 mg/kg body weight, or of about 20 mg/kg body weight, or of about 22.5 mg/kg body weight, or of about 24 mg/kg body weight, or of about 25 mg/kg body weight, or of about 27.5 mg/kg body weight, or of about 30 mg/kg body weight, or of about 32.5 mg/kg body weight, or of about 35 mg/kg body weight, or of about 37.5 mg/kg body weight, or of about 40 mg/kg body weight, or of about 45 mg/kg body weight, or of about 50 mg/kg body weight, or of about 55 mg/kg body weight, or of about 60 mg/kg body weight, or of about 65 mg/kg body weight, or of about 70 mg/kg body weight, or of about 80 mg/kg body weight, or of about 85 mg/kg body weight, or of about 90 mg/kg body weight, or of about 95 mg/kg body weight, or of about 100 mg/kg body weight, or of about 110 mg/kg body weight, or of about 115 mg/kg body weight, or of about 120 mg/kg body weight, or of about 125 mg/kg body weight, or of about 130 mg/kg body weight, or of about 135 mg/kg body weight, or of about 140 mg/kg body weight, or of about 145 mg/kg body weight, or of about 150 mg/kg body weight, or of about 155 mg/kg body weight, or of about 160 mg/kg body weight, or of about, or of about 165 mg/kg body weight, 170 mg/kg body weight, or of about 175 mg/kg body weight, or of about 180 mg/kg body weight, or of about 190 mg/kg body weight, or of about 200 mg/kg body weight.

Most preferably, a dosage unit of the pharmaceutical composition as defined herein or the medicament comprising the extract as defined herein, comprises from 50 to 5000 mg of the extract, preferably from 200 to 3500 mg, more preferably from 300 to 2500 mg, even more preferably from 400 to 2000 mg, or most preferably from 250 to 1500 mg, and is preferably administered at least once a day or one to four times a day, preferably once, twice, three times or four times a day.

The present invention further concerns a method of treatment and/or prevention of a disease, wherein the method comprises administering to a subject in need thereof a therapeutically effective amount of the pharmaceutical composition as defined herein or the medicament comprising the extract as defined herein.

Preferably, the method of treatment and/or prevention of a disease as defined herein is a method of treatment and/or prevention of a disease selected from the group consisting of a neurodegenerative disease, an inflammatory disease, an autoimmune disease, a tumour disease and a protozoan infectious disease. More preferably, the method of treatment and/or prevention according to the present invention is a method of treatment and/or prevention of multiple sclerosis, amyotrophic lateral sclerosis, morbus Crohn, psoriasis, atopic dermatitis, lichen planus, glioblastoma, peritumoral edema, rheumatic diseases, respiratory diseases or lupus erythematodes.

The method of treatment and/or prevention of a disease according to the present invention is preferably characterized by the features described herein with respect to the use of the pharmaceutical composition and the medicament comprising the inventive extract.

In a further aspect, the present invention provides a cosmetic composition, which comprises the extract according to the present invention. Further, the present invention concerns the use of the inventive extract in a cosmetic composition. The cosmetic composition according to the present invention comprises the inventive extract and at least one additional ingredient suitable for cosmetic use. Preferably, the additional ingredient is selected from the group consisting of emulsifiers, surfactants, preservatives, antioxidants, thickening agents, perfumes or dyes.

The cosmetic composition according to the present invention (or, alternatively, the pharmaceutical composition as defined herein) is preferably used for the cosmetic treatment of irritated or stressed skin. Therein, the cosmetic composition preferably alleviates the skin irritation, calms the respective skin and/or re-vitalizes the skin. The cosmetic composition according to the invention is preferably provided in a form, which is suitable for topical administration, preferably as an aqueous or oily solution or suspension; a liposomal formulation; an emulsion; a dermal patch, an ointment; a cream; a gel; or a lotion. The cosmetic composition is preferably suitable for us as a lotion, a cream, a gel, a shampoo, a soap, a dermal patch, a mask, a deodorant, an after shave or the like. In a preferred embodiment, the cosmetic composition is a lipophilic composition, preferably comprising the inventive extract and at least one lipid cosmetic excipient. Preferably, the cosmetic composition is formulated as a liposomal composition (e.g. a liposomal suspension in an aqueous phase).

In another aspect, the present invention concerns a food supplement comprising the *Boswellia* extract according to the present invention. As used herein, the term 'food supplement' is to be understood in a broad sense as any ingestible food product capable of supplementing the normal diet of an individual. For example, the food supplement according to the present invention may comprise the category of "dietary foods for special medical purposes" as provided in the Commission Directive 1999/21/EC. Accordingly, the food supplement may be provided in oral dosage form suitable for oral administration, for example, as capsules, preferably gelatine capsules, more preferably soft gelatine capsules, tablets, troches, lozenges, aqueous or oily suspensions or solutions, dispersible powders or granules, emulsions, hard or soft capsules, or syrups or elixirs, which may further comprise one or more additives, such as e.g. flavouring or sweetening agents, such as saccharine, or sorbitol, or antioxidants. The food supplement as defined above may be administered in any amount, e.g. in any amount as defined above.

In a further aspect, the present invention provides a dietary supplement. The dietary supplement may be provided in solid or in liquid form, e.g. as a powder, capsules, preferably gelatine capsules, more preferably soft gelatine capsules, a liquid or a gel, or any other suitable form, which may further comprise one or more additives such as e.g. flavouring or sweetening agents, such as saccharine, or sorbitol. The dietary supplement according to the invention may be added to a wide array of foodstuffs, but without significantly altering the foodstuff's taste, odour and/or consistency. The term 'foodstuff' as used in the context of the present invention may be used to refer to a food or a beverage, for example, carbonated beverages, water e.g., bottled water, mineral water, sparkling water, tap water, and the like, fruit juices, vegetable juices, milk, sports drinks, cooking oils, salad dressings, condiments, soups, granola or energy bars. Thus, the foodstuffs may be in fluid form, or they may be in a more solid form. The dietary supplement of the present invention may also be provided in oral dosage forms suitable for oral administration, for example, as capsules, tablets, troches, lozenges, aqueous or oily suspensions or solutions, dispersible powders or granules, emulsions, hard or soft capsules, or syrups or elixirs, in any amount, such as e.g. those provided above.

In another aspect, the present invention provides a food or a beverage comprising the *Boswellia* extract according to the invention. As used herein, the terms 'food' and 'beverage' refer to any ingestible food product in solid, liquid or semi-liquid/semi-solid form. The extract according to the invention is typically admixed in the manufacturing process of a food or beverage or added to the final food or beverage product.

BRIEF DESCRIPTION OF THE FIGURES

The Figures shown in the following are merely illustrative and shall describe the present invention in a further way. These Figures shall not be construed to limit the present invention thereto.

EXAMPLES

Figure 1:
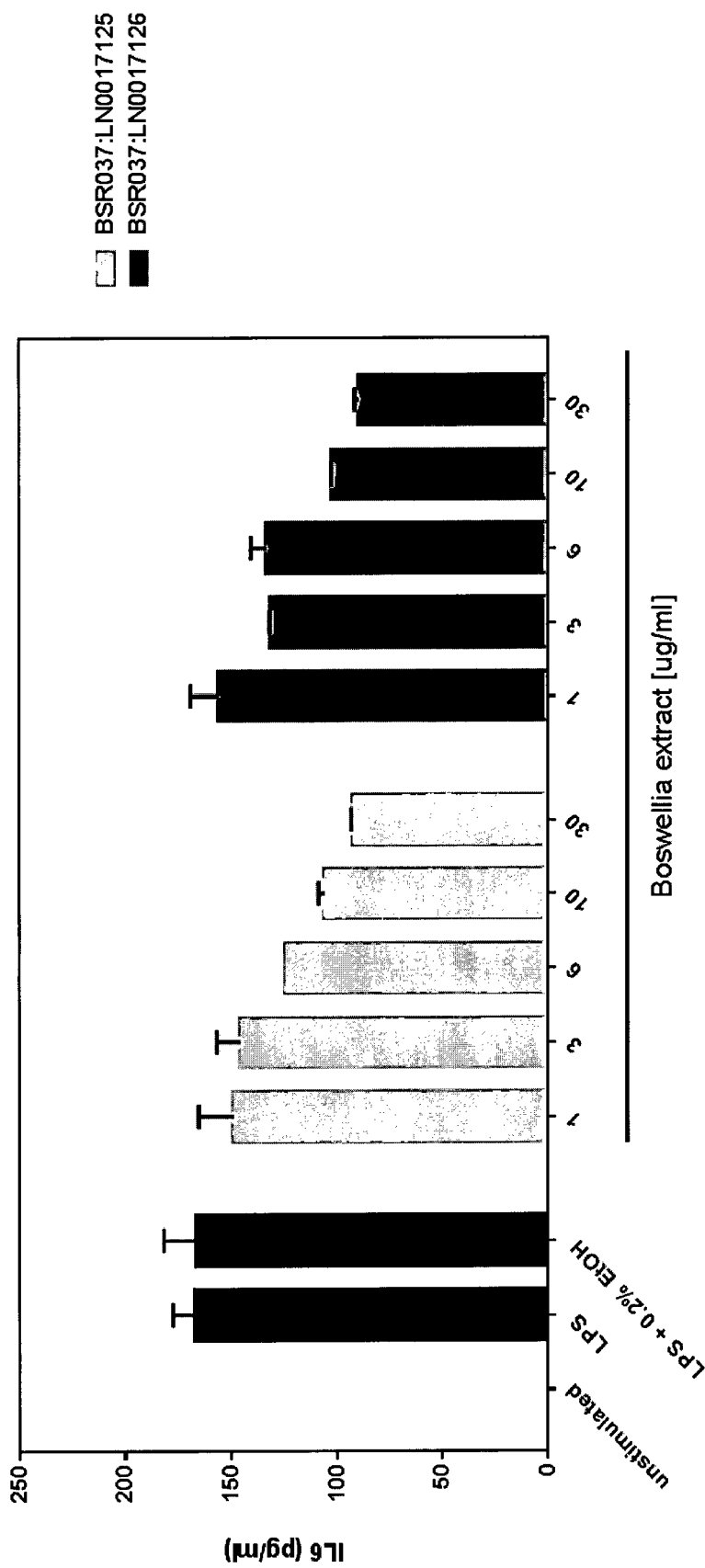
FIG. 1: Effect of *Boswellia* extracts on LPS-stimulated IL6 release in THP-1 cells

The following Examples are intended to illustrate the invention further. They are not intended to limit the subject matter of the invention thereto.

The examples and results provided herein are based on data obtained using resin extracts prepared with ethanol/water as extraction solvent as defined in the ESCOP Monograph for Olibanum indicum (Olibanum indicum). Resins from India (*Boswellia serrata* Roxb.ex Colebr., examples 3 and 10), Somalia (*Boswellia carteri* syn. *sacra* Birdwood, Example 6), Oman (*Boswellia sacra* syn. *carteri* Birdwood, Example 1), served as starting materials. The obtained standard ethanolic liquid extracts (Examples 1, 3, 6, and 10) were analyzed on their content of undesired compounds as well as on their content of boswellic acids and cembrenes. The extract from Example 10 was also processed using state of the art procedures to obtain a standard solvent free dry powder extract (Example 14) or a standard solvent free oily extract (Example 15). Further this extract and the extracts of Examples 1, 3 and 6 were also purified according to the inventive process to obtain the new extract composition.

Briefly, standard ethanolic liquid extracts were prepared (Examples 1, 3, 6 and 10), which underwent an evaporation step followed by adjusting the Ethanol content of the resulting concentrate to an ethanol concentration between 20 and 50% (w/w) ethanol (this process step results in first reduction of the undesired volatile oil compounds). The resulting suspension was purified from protein interacting polyphenols by addition of an aqueous solution of gelatin (tannin-gelatin crosslinking reaction, also called hardening) and subsequently cellulose powder was added, which binds the protein-polyphenol-complexes to form a fine dispersion (the suspended cellulose particles hydrate and are form little granules with the gelatin and the polyphenol crosslinked gelatin resulting in a fine disperse hydrophilic adsorbate). In the following, ethanol was added until a concentration of 80-90% (w/w) was reached (the addition of ethanol leads to dehydration and precipitation of the granules on the one side and dissolving of the lipophilic extractives on the other side). A precipitate and a clear supernatant were obtained, the latter representing the purified extract solution. The supernatant was separated from the precipitate by filtration in order to obtain a clear purified ethanolic liquid extract (Examples 2, 4, 7 and 11) as a process intermediate. Typically, the filtration was done in two steps: a first filtration for obtaining a clear liquid and a second filtration after mixing the extract solution with diatomaceous earth (Celite®), which binds potentially remained traces of non-precipitated gelatin. Said extract solution was subjected to an initial evaporation step followed, after water addition, by a water steam distillation at 90-100° C. In some examples, this process was carried out in the presence of an additionally added lipid phase, which protects cyclic diterpenoids, namely monocyclic diterpenoids, such as cembranoids, but not the undesired mono and sesquiterpenes, from evaporation during steam distillation. During said process step, residues of undesired steam volatile compounds (mono- and sesquiterpens) evaporated together with the water steam and were so eliminated from the extract solution. Finally, the remaining solution was evaporated at 40-70° C. until the it was solvent free. Subsequently the purified solvent free oily liquid extract (Example 5, 8 and 12) or the purified solvent free dry powder extract (Example 9 and 13) was obtained.

Material and Methods

The following examples illustrate the present invention. Beside the detailed description of the extraction and purification procedures and their yields the resulting intermediate extracts and finished extracts were analyzed on their content of limonene, linalool, thujone and estragol, their content of serratol, incensol and incensol-acetate as well as boswellic acids (see Table 1). The intermediate products were analyzed additionally on their content of polyphenolic compounds. The analysis of mono- and sesquiterpenes was performed by Labor Veritas, Engimattstrasse, Zürich, Switzerland using gas chromatography coupled to MS readout (Labor Veritas GC-Reports No 214-0721), whereas the analysis of pentacyclic triterpenic boswellic acids (11-keto-ß-boswellic-acid (KBA), acetyl-11-keto-ß-boswellic acid (AKBA), ß-boswellic-acid, acetyl-ß-boswellic-acid, α-boswellic-acid and acetyl-α-boswellic-acid have been measured individually and been additively mentioned as "triterpenic acids" in the following examples) and cembrenes (serratol, incensole and incensole-acetate have been measured individually and been additively mentioned as "cembrenes" in the following examples) was performed in house by high pressure liquid chromatography (Method/Top Alpinia No. TOP-215: reports no. SR-2029) and the analysis of polyphenol was performed in house by UV/VIS spectroscopy according to the method in the European Pharmacopoe 7.0/2.08.14.00, in house reports no.: AR-1131. The following resins were used for the experiments: Example 1 and 2 OBM001 (*Boswellia sacra*, Oman); Examples 3, 4 and 5 OBN001 (*Boswellia serrata*, India), Examples 6, 7, 8, 9 BAX019 (*Boswellia carteri*, Somalia) and Examples 10, 11, 12, 13, 14 and 15 BSR037 (*Boswellia serrata*, India), documented in in-house release documents AR-1065.01, 1037.01, 1097.01, 1096.01, 1128.01, and 1091.01. Unless otherwise specified, the percentages indicated in the Examples refer to weight percent (% w/w).

Example 1 (Preparation of a Standard Ethanolic Liquid Extract OBM001: LN00226)

20.0 g milled resin (particle size <2 mm) were extracted with 200.01 g Ethanol 80% w/w in an 500 ml Erlenmeyer under stirring at 250 rpm, 50° C. for 60 min. The preparation was then filtrated twice over a deep layer cellulose filter (AF15 Filtrox®).

Results: 184.54 g of a clear amber liquid extract with a solid content (dry weight of the extract after evaporation) of 6.54% were obtained. A sample of the extract was analyzed and the following content (calculated based on the dry weight of the standard ethanolic liquid extract obtained in Example 1) was obtained: estragol: 138.2 ppm; linalool: 98.1 ppm; limonene: 12.6 ppm; thujone: 34.8 ppm (gas chromatography); triterpenic acids: 21.49% (HPLC); cembrenes: 4.18% (HPLC) and polyphenols (Ph.Eur.): 0.19% (spectrophotometry).

Example 2 (Preparation of a Purified Ethanolic Liquid Extract OBM001:LN00227)

50.1 g of the liquid extract from Example 1 (OBM001: LN00226) was transferred to a 250 ml glass flask and 75-85% of the solvent was evaporated at 150 mbar, 100 rpm and 60° C. until an residual suspension of 15-25%, calculated to the starting amount, was reached. The flask was transferred to a balance and ethanol 40% w/w was added until a total filling weight of 25 g was reached. A clear amber liquid was obtained. Subsequently 5.2 g cellulose powder (Sanacel®) and 6.7 g of a gelatin solution (gelatin Ph.Eur.: 10% w/w aqueous solution) were added and rotated at 60° C. and 100 rpm for 45 min. After said time 110 g of ethanolum absolutum (PhEur.) were added and rotated at 100 rpm, 20-30° C. for 15 min. The mixture was filtered twice over a deep layer cellulose filter (AF15 Filtrox®) and a clear yellowish liquid extract was obtained (117.5 g). Said extract was transferred in a 250 ml glass flask and 2.0 g of a diatomaceous earth (Celite®) were added. This suspension was rotated at 20-30° C. for 10 min and was then filtered twice over a deep layer cellulose filter (AF50 Filtrox®).

Results: 106.8 g of a clear yellowish liquid extract with a solid content (dry weight of the extract after evaporation) of 2.49% was obtained. A sample of the extract was analyzed and the following content (calculated based on the dry weight of the extract obtained in Example 2) was obtained: estragol: 103.8 ppm; linalool: 179.6 ppm; limonene: <10.0 ppm; thujone: 33.3 ppm (gas chromatography); triterpenic acids: 23.90% (HPLC); cembrenes: 4.63% (HPLC) and Polyphenols (Ph.Eur.): 0.00% (spectrophotometry). Compared to the standard extract, 111% of triterpenic acids and 111% of cembrenes were resulting.

Example 3 (Preparation of a Standard Ethanolic Liquid Extract OBN001: LN00228)

20.03 g milled resin (particle size <2 mm) were extracted with 200.01 g Ethanol 80% w/w in an 500 ml Erlenmeyer under stirring at 250 rpm, 50° C. for 60 min. The preparation was then filtrated twice over a deep layer cellulose filter (AF15 Filtrox®).

Results: 191.41 g of a clear amber liquid extract with a solid content (dry weight of the extract after evaporation) of 6.31% were obtained. A sample of the extract was analyzed and the following content (calculated based on the dry weight of standard ethanolic liquid extract obtained in Example 3) was obtained: estragol: 7388.6 ppm; Linalool: 481.3 ppm; Limonene: <5.0 ppm; thujone: 14.5 ppm (gas chromatography); triterpenic acids: 27.46% (HPLC); cembrenes: 8.62% (HPLC).

Example 4 (Preparation of a Purified Ethanolic Liquid Extract OBN001:LN00228.1)

50.1 g of the liquid extract from Example 3 (OBN001: LN00228) were transferred to a 250 ml glass flask and 75-85% of the solvent were evaporated at 150 mbar, 100 rpm and 60° C. until an residual suspension of 15-25%, calculated to the starting amount, was reached. The flask was transferred to a balance and ethanol 40% w/w was added until a total filling weight of 25 g was reached. A clear amber liquid was obtained. Subsequently 5.2 g cellulose powder (Sanacel®—to form granules with precipitating gelatin) was suspended in the liquid and then 6.7 g of a gelatin solution (gelatin Ph.Eur.: 10% w/w aqueous solution) were dissolved and rotated at 60° C. and 100 rpm for 45 min. After said time, 110 g of ethanolum absolutum (PhEur.) were added and the mixture was rotated at 100 rpm, 20-30° C. for 15 min, resulting in a fine disperse precipitate and a clear supernatant. The mixture was filtered twice over a deep layer cellulose filter (AF15 Filtrox®) and a clear yellowish liquid extract was obtained (117.5 g). Said extract was transferred in a 250 ml glass flask and 2.0 g of a diatomaceous earth (Celite®—to bind residual traces of gelatin) were added. This suspension was rotated at 20-30° C. for 10 min and then filtered twice over a deep layer cellulose filter (AF50 Filtrox®).

Results: 110.2 g of a clear yellowish liquid extract with a solid content (dry weight of the extract after evaporation) of 2.44% was obtained. A sample of the extract was analyzed and the following content (calculated based on the dry weight of the extract obtained in Example 4) was obtained: estragol: 3218.3 ppm; linalool: 391.3 ppm; limonene: <10.0 ppm; thujone: <10.0 ppm (gas chromatography); triterpenic acids: 27.77% (HPLC); cembrenes: 8.76 (HPLC). Compared to the standard extract, 101% of triterpenic acids and 102% of cembrenes were resulting.

Example 5 (Preparation of a Purified Solvent Free Oily Liquid Extract OBN001:LN002211.2)

75.0 g of the purified ethanolic liquid extract from Example 4 (OBN001:LN0228) were transferred to a 250 ml glass flask and 1.68 g middle-chain triglycerides (Labrafac®- to dissolve the extractives and prevent evaporation of diterpenoids) plus 0.545 g middle chain mono and diglycerides (Peceol®- to dissolve the extractives and prevent evaporation of diterpenoids) were added. The mixture was evaporated under reduced pressure at 200 mbar, 250 rpm and 55° C. for 20 min. Then 60.0 g of distilled water (steam distillation of mono and sesquiterpenes) were added and distillation was started at 600 mbar, 90° C. for 30 min. Subsequently, the vacuum was reduced to 200 mbar and evaporation was performed for further 30 min. Then the bath temperature was reduced to 50° C. and the residual solvent was evaporated at 150-5 mbar during an additional time of 60 min.

Results: 4.05 g of a viscous clear amber liquid extract were obtained. A sample of the extract was analyzed and the following content (calculated based on the dry weight of the purified ethanolic liquid extract (i.e. 75.0 g×0.0244=1.83 g)

obtained in Example 4) was obtained: estragol: 76.7 ppm; linalool: 15.0 ppm; limonene: <5.0 ppm; thujone: <5.0 ppm (gas chromatography); triterpenic acids: 27.13% (HPLC); cembrenes: 10.62% (HPLC). Compared to the standard ethanolic liquid extract of Example 3, 99% of triterpenic acids and 123% of cembrenes were resulting.

Example 6 (Preparation of a Standard Ethanolic Liquid Extract BAX019: LN0017127)

100.20 g milled resin (particle size <1 mm) were extracted with 1001.14 g ethanol 80% w/w in an 2000 ml Erlenmeyer under stirring at 250 rpm, 50° C. for 90 min. The preparation was then filtered twice over a deep layer cellulose filter (Beco® Filter CPKS) after addition of 8.0 g crospovidone (Ph.Eur.) and 17.14 g Sanacel®.

Results: 974.31 g of a clear amber liquid extract with a solid content (dry weight of the extract after evaporation) of 5.57% were obtained. A sample of the extract was analyzed and the following content (calculated based on the dry weight of the standard ethanolic liquid extract obtained in Example 6) was obtained: estragol: 36.0 ppm; linalool: 40.2 ppm; limonene: <12.0 ppm; thujone: 60.0 ppm (gas chromatography); triterpenic acids: 21.06% (HPLC); cembrenes: 21.14% (HPLC) and polyphenols (Ph.Eur.): 0.41% (spectrophotometry).

Example 7 (Preparation of a Purified Ethanolic Liquid Extract BAX019:LN0017128)

500.24 g of the liquid extract from Example 6 (BAX019: LN0017127) were transferred to a 2000 ml glass flask and 75-85% of the solvent were evaporated at 150 mbar, 100 rpm and 60° C. until an residual suspension of 15-25%, calculated to the starting amount, was reached. The flask was transferred to a balance and ethanol 40% (w/w) was added until a total filling weight of 250 g was reached. A clear amber liquid was obtained. Subsequently, 50.31 g cellulose powder (Sanacel®) and 67.10 g of a gelatin solution (gelatin Ph.Eur.: 20% w/w aqueous solution) were added and rotated at 60° C. and 100 rpm for 30 min. After said time, 1108.38 g of ethanolum absolutum (PhEur.) were added and rotated at 100 rpm, 20-30° C. for 15 min. The mixture was filtered twice over a deep layer cellulose filter (AF15 Filtrox®) and a clear yellowish liquid extract was obtained. Said extract was transferred in a 2000 ml glass flask and 20.6 g of a diatomaceous earth (Celite®) were added. This suspension was rotated at 20-30° C. for 10 min and then filtered over a deep layer cellulose filter (AF50 Filtrox®).

Results: 1090.97 g of a clear yellowish liquid extract with a solid content (dry weight of the extract after evaporation) of 1.91% were obtained. A sample of the extract was analyzed and the following content (calculated based on the dry weight of the purified ethanolic liquid extract obtained in Example 7) was obtained: estragol: 36.0 ppm; linalool: 52.8 ppm; limonene: <12.0 ppm; thujone: <12.0 ppm (gas chromatography); triterpenic acids: 22.57% (HPLC); cembrenes: 22.75% (HPLC) and polyphenols (Ph.Eur.): 0.08 (spectrophotometry). Compared to the standard ethanolic liquid extract of Example 6, 107% of triterpenic acids and 108% of cembrenes were resulting.

Example 8 (Preparation of a Purified Solvent Free Oily Liquid Extract BAX019:LN0017132)

200.03 g of the purified ethanolic liquid extract from Example 7 (BAX019:LN0017128) were transferred to a 500 ml glass flask and 0.97 g middle-chain triglycerides (Labrafac®) plus 0.97 g middle chain mono and diglycerides (Peceol®) were added. The mixture was evaporated under reduced pressure at 200 mbar, 250 rpm and 60° C. for 30 min. Then 45.0 g of distilled water were added and distillation was started at 900 mbar for 30 min, then 600 mbar, 90° C. for 30 min. Subsequently, the vacuum was reduced to 200 mbar and evaporation was performed for further 20 min. Then the bath temperature was reduced to 60° C. and the residual solvent was evaporated at 150-5 mbar during an additional time of 60 min.

Results: 5.89 g of a viscous clear amber liquid extract were obtained. A sample of the extract was analyzed and the following content (calculated based on the dry weight of the purified ethanolic liquid extract (i.e. 200.03 g×0.0191=3.82 g) obtained in Example 7) was obtained: estragol: 11.6 ppm; linalool: <5.0 ppm; limonene: <5.0 ppm; thujone: <5.0 ppm (gas chromatography); triterpenic acids: 20.33% (HPLC); cembrenes: 19.44% (HPLC). Compared to the standard ethanolic liquid extract of Example 6, 97% of triterpenic acids and 92% of cembrenes were resulting. The polyphenol content of the extract of Example 8 is 0.08%, as the extract is prepared from the extract obtained in Example 7.

Example 9 (Preparation of a Purified Solvent Free Dry Powder Extract BAX019:LN0017130)

200.09 g of the purified ethanolic liquid extract from Example 7 (BAX019:LN0017128) were transferred to a 250 ml glass flask. The extract solution was evaporated under reduced pressure at 200 mbar, 250 rpm and 60° C. for 60 min. Then 45.0 g of distilled water were added and distillation was started at 900 mbar for 30 min, then 600 mbar, 90° C. for 30 min. Subsequently, the vacuum was reduced to 200 mbar and evaporation was performed for further 20 min. Then the bath temperature was reduced to 60° C. and the residual solvent was evaporated at 150-5 mbar during an additional time of 60 min.

Results: 4.31 g of a yellow powder were obtained. A sample of the extract powder was analyzed and the following content (calculated based on the dry weight of the purified ethanolic liquid extract (i.e. 200.09 g×0.0191=3.82 g) obtained in Example 7) was obtained: estragol: 17.8 ppm; linalool: <11.5 ppm; limonene: <5.0 ppm; thujone: 17.1 ppm (gas chromatography); triterpenic acids: 18.92% (HPLC); cembrenes: 18.45% (HPLC). Compared to the standard ethanolic liquid extract of Example 6, 90% of triterpenic acids and 87% of cembrenes were resulting.

Example 10 (Preparation of a Standard Ethanolic Liquid Extract BSR037: LN0017121)

100.87 g milled resin (particle size <1 mm) were extracted with 1000.14 g ethanol 80% w/w in a 2000 ml Erlenmeyer under stirring at 250 rpm, 50° C. for 90 min. The preparation was then filtered twice over a deep layer cellulose filter (Beco® Filter CPKS) after addition of 8.02 g crospovidone (Ph.Eur.) and 17.02 g Sanacel®.

Results: 962.09 g of a clear amber liquid extract with a solid content (dry weight of the extract after evaporation) of 5.98% were obtained. A sample of the extract was analyzed and the following content (calculated based on the dry weight of the standard ethanolic liquid extract obtained in Example 10) was obtained: estragol: 3987.3 ppm; linalool: 367.0 ppm; limonene: 11.9 ppm; thujone: 86.7 ppm (gas chromatography); triterpenic acids: 24.02% (HPLC); cembrenes: 9.16% (HPLC) and polyphenols (Ph.Eur.): 0.05 (spectrophotometry).

Example 11 (Preparation of a Purified Ethanolic Liquid Extract BSR037:LN0017122)

500.10 g of the liquid extract from example 10 (BSR037: LN0017121) were transferred to a 2000 ml glass flask and 75-85% of the solvent was evaporated at 150 mbar, 100 rpm and 60° C. until an residual suspension of 15-25%, calculated to the starting amount, was reached. The flask was transferred to a balance and ethanol 40% w/w was added until a total filling weight of 250 g was reached. A clear amber liquid was obtained. Subsequently, 50.3 g cellulose powder (Sanacel®) and 67.2 g of a gelatin solution (gelatin Ph.Eur.: 10 w/w aqueous solution) were added and rotated at 60° C. and 100 rpm for 30 min. After said time, 1100.8 g of ethanolum absolutum (PhEur.) were added and rotated at 100 rpm, 30° C. for 30 min. The mixture was filtered twice over a deep layer cellulose filter (AF15 Filtrox®) and a clear yellowish liquid extract was obtained. Said extract was transferred to a 2000 ml glass flask and 20.0 g of a diatomaceous earth (Celite®) were added. This suspension was rotated at 20-30° C. for 10 min and then filtered over a deep layer cellulose filter (AF50 Filtrox®).

Results: 931.55 g of a clear yellowish liquid extract with a solid content (dry weight of the extract after evaporation) of 1.84% were obtained. A sample of the extract was analyzed and the following content (calculated based on the dry weight of the extract obtained in Example 11) was obtained: estragol: 2482.2 ppm; linalool: 281.1 ppm; limonene: <13.0 ppm; thujone: 27.0 ppm (gas chromatography); triterpenic acids: 26.37% (HPLC); cembrenes: 9.05% (HPLC) and polyphenols (Ph.Eur.): 0.00% (spectrophotometry). Compared to the standard ethanolic liquid extract of Example 10, 110% of triterpenic acids and 99% of cembrenes were resulting.

Example 12 (Preparation of a Purified Solvent Free Oily Liquid Extract BSR037:LN0017125)

200.02 g of the purified ethanolic liquid extract from Example 11 (BSR037:LN0017122) were transferred to a 500 ml glass flask and 0.96 g middle-chain triglycerides (Labrafac®) plus 0.96 g middle chain mono and diglycerides (Peceol®) were added. The mixture was evaporated under reduced pressure at 200 mbar, 250 rpm and 60° C. for 30 min. Then 45.0 g of distilled water were added and distillation was started at 900 mbar, 90° C. for 30 min, then 600 m bar, 90° C. for 30 min. Subsequently, the vacuum was reduced to 200 mbar and evaporation was performed for further 20 min. Then the bath temperature was reduced to 60° C. and the residual solvent was evaporated at 150-5 mbar during an additional time of 60 min.

Results: 6.10 g of a viscous clear amber liquid extract were obtained. A sample of the extract was analyzed and the following content (calculated based on the dry weight of the purified ethanolic liquid extract (i.e. 200.02 g×0.0184=3.68 g) obtained in Example 11) was obtained: estragol: 65.1 ppm; linalool: 12.6 ppm; limonene: <5.0 ppm; thujone: 9.5 ppm (gas chromatography); triterpenic acids: 24.10% (HPLC); cembrenes: 9.02% (HPLC). Compared to the standard ethanolic liquid extract of Example 10, 100% of triterpenic acids and 98% of cembrenes were resulting. The polyphenol content of the extract of Example 12 is 0%, as the extract is prepared from the extract obtained in Example 11.

Example 13 (Preparation of a Purified Solvent Free Dry Powder Extract BSR037:LN0017124)

200.4 g of the purified ethanolic liquid extract from Example 11 (BSR037:LN0017122) were transferred to a 500 ml glass flask. The extract solution was evaporated under reduced pressure at 200 mbar, 250 rpm and 60° C. for 60 min. Then 45.0 g of distilled water were added and distillation was started at 900 mbar at 90° C. for 30 min, then 600 mbar, 90° C. for 30 min. Subsequently, the vacuum was reduced to 200 mbar and evaporation was performed for further 20 min. Then the bath temperature was reduced to 60° C. and the residual solvent was evaporated at 150-5 mbar during an additional time of 60 min.

Results: 3.95 g of a yellow dry powder were obtained. A sample of the extract powder was analyzed and the following content (calculated based on the dry weight of the purified ethanolic liquid extract (i.e. 200.04 g×0.0184 g=3.68 g) obtained in Example 11) was obtained: estragol: 281.1 ppm; linalool: 96.2 ppm; limonene: <10.0 ppm; thujone: 17.1 ppm (gas chromatography); triterpenic acids: 22.20% (HPLC); cembrenes: 8.41% (HPLC).). Compared to the standard ethanolic liquid extract of Example 10, 92% of triterpenic acids and 92% of cembrenes were resulting.

Example 14 (Preparation of a Standard Solvent Free Dry Powder Extract BSR037:LN0017123)

109.10 g of the standard ethanolic liquid extract from Example 10 (BSR037: LN0017121) were transferred to a 250 ml glass flask. The extract solution was evaporated under reduced pressure at 200 mbar, 250 rpm and 60° C. for 60 min. Subsequently, the vacuum was reduced to 150 mbar and evaporation was performed for an additional time of 60 min.

Results: 6.05 g of a yellow powder were obtained. A sample of the extract powder was analyzed and the following content (calculated based on the dry weight of the standard ethanolic liquid extract (i.e. 109.10 g×0.0598=6.52 g) obtained in Example 10) was obtained: estragol: 2777.2 ppm; linalool: 325.1 ppm; limonene: 18.0 ppm; thujone: 27.0 ppm (gas chromatography); triterpenic acids: 22.29% (HPLC); cembrenes: 8.40% (HPLC). Compared to the standard ethanolic liquid extract of Example 10, 93% of triterpenic acids and 92% of cembrenes were resulting.

Example 15 (Preparation of a Standard Solvent Free Oily Extract BSR037:LN0017126)

100.00 g of the standard ethanolic liquid extract from Example 10 (BSR037: LN0017121) were transferred to a 250 ml glass flask and 1.49 g middle-chain triglycerides (Labrafac®) plus 1.49 g middle chain mono and diglycerides (Peceol®) were added. The mixture was evaporated under reduced pressure at 600 mbar, 250 rpm and 60° C. and then the vacuum was reduced to 10 mbar in the course of 50 min and the final vacuum was maintained at 60° C. and 250 rpm for 15 min.

Results: 9.27 g of a viscous clear amber liquid extract were obtained. A sample of the extract powder was analyzed and the following content (calculated based on the dry weight of the standard ethanolic liquid extract (i.e. 100.00 g×0.0598=5.98 g) obtained in Example 10 (100.00 g×0.0598=5.98 g)) was obtained: estragol: 1156.6 ppm; linalool: 176.7 ppm; limonene: <10.0 ppm; thujone: 15.7 ppm (gas chromatography); triterpenic acids: 22.83% (HPLC); cembrenes: 8.69% (HPLC). Compared to the standard ethanolic liquid extract of Example 10, 95% of triterpenic acids and 95% of cembrenes were resulting.

vides extracts from the resins of *Boswellia* species, wherein undesired volatile mono- and sesquiterpenoids as well as polyphenolic compounds are reduced or eliminated, while it retains desired secondary plant metabolites of Olibanum, namely triterpenic acids as well as cyclic diterpenoids, such as the group of cembrenes.

TABLE 1

Summary of the analysis results

| | | | undesired compounds | | | | | desired compounds | |
| | | | | | | | | Triterpenic | |
| Ex. derived | Extract type | resin type | Estragol (ppm) | Linalool (ppm) | Limonene (ppm) | Thujone (ppm) | Polyphenols (% w/w) | acids (% w/w) | Cembrenes (% w/w) |
|---|---|---|---|---|---|---|---|---|---|
| 1 | SEL | Arabian sacra | 138.2 | 98.1 | 12.6 | 34.8 | 0.19 | 21.49 | 4.18 |
| 2 (from 1) | PEL | Arabian sacra | 103.8 | 179.6 | <10 | 33.3 | 0 | 23.9 | 4.63 |
| 3 | SEL | Indian serrata | 7388.6 | 481.3 | <5 | 14.5 | n.d. | 27.46 | 8.62 |
| 4 (from 3) | PEL | Indian serrata | 3218.3 | 391.3 | <10 | <10 | n.d. | 27.77 | 8.76 |
| 5 (from 4) | POL | Indian serrata | 76.7 | 15 | <5 | <5 | 0 | 27.13 | 10.62 |
| 6 | SEL | Somalia carteri | 36 | 40.2 | <12 | 60 | 0.41 | 21.06 | 21.14 |
| 7 (from 6) | PEL | Somalia carteri | 36 | 52.8 | <12 | <12 | 0.08 | 22.57 | 22.75 |
| 8 (from 7) | POL | Somalia carteri | 11.6 | <5 | <5 | <5 | <0.08 | 20.33 | 19.44 |
| 9 (from 7) | PDP | Somalia carteri | 17.8 | 11.5 | <5 | 17.1 | n.d. | 18.92 | 18.45 |
| 10 | SEL | Indian serrata | 3987.3 | 367 | 11.9 | 86.7 | 0.05 | 24.02 | 9.16 |
| 11 (from 10) | PEL | Indian serrata | 2482.2 | 281.1 | <13 | 27 | 0 | 26.37 | 9.05 |
| 12 (from 11) | POL | Indian serrata | 65.1 | 12.6 | <5 | 9.5 | 0 | 24.1 | 9.02 |
| 13 (from 11) | PDP | Indian serrata | 281.1 | 96.2 | <10 | 17.1 | n.d. | 22.2 | 8.41 |
| 14 (from 10) | SDP | Indian serrata | 2777.2 | 325.1 | 18 | 27 | n.d. | 22.29 | 8.4 |
| 15 (from 10) | SOL | Indian serrata | 1156.6 | 176.7 | <10 | 15.7 | n.d. | 22.83 | 8.69 |

(SEL: standard ethanolic liquid extract; PEL: purified ethanolic liquid extract; POL: purified solvent free oily liquid extract; PDP: purified solvent free dry powder extract; SDP: standard solvent free dry powder extract)

CONCLUSIONS

As shown in the technological Examples 2, 4, 7, and 11 *Boswellia* extracts processed with the new purification process methodology, already the purified liquid extracts (intermediate step of the process) show reductions of limonene, linalool and thujone as well as estragol and also show very low levels or even absence of protein interacting polyphenols when normalized to the differing initial load of polyphenols of the standard extracts of Examples 1, 3, 6, and 10. Furthermore, the final extracts prepared according to the inventive process (oily extract Examples 5, 8 and 12) contain less than 20 ppm of each of limonene, linalool and thujone and less than 100 ppm of estragol. Also the purified dry powder extracts (Examples 9 and 13) contain considerably lower amounts of the undesired compounds than the standard extracts. The purified extracts also show very low levels of protein interacting polyphenols and, importantly, with small deviations between the different examples, independently of the initial load of polyphenols in the standard extracts. On the other hand, the inventive process retains the desired secondary plant metabolites of Olibanum, namely the triterpenic acids as well as the cyclic diterpenoids such as cembrenes (>90% w/w of the standard extract content) in the extract up to the final oily extracts (Examples 5, 8 and 12), and in the purified dry powder extracts (Example 9 and 13 with at least 87% recovery of triterpenic acids). These results reflect the robustness and validity of the process of the present invention with respect to the production of novel *Boswellia* extracts free or nearly free of undesired compounds. The process according to the invention thus pro- Example 16 (Cytokine Analysis in Lipopolysaccharide-Stimulated THP-1 Cells)

THP-1 cells were stimulated with lipopolysaccharide (LPS) and cytokine levels were measured after incubation with *Boswellia* extract BSR037: LN00125 (Example 12) or *Boswellia* extract BSR037: LN00126 (Example 15).

THP-1 cells (ATCC® TIB202™), a human monocyte cell line (from acute monocytic leukemia), were cultured in RPMI-1640 Medium (Lonza) supplemented with 10% Fetal Bovine Serum (Life Technologies), 0.05 mM 2-mercaptoethanol (Life Technologies), 4.5 g/L glucose (Sigma), 10 mM HEPES (Sigma), and 1 mM sodium pyruvate (Sigma).

In 96 well round-bottom plates (cell culture treated), 7×105 THP-1 cells per well were plated in 180 μl/well THP-1 medium. Cells were incubated for 1-2 hours at 37° C. and 5% $CO_2$ until extract dilutions were ready. Dilutions of extracts and ethanol (as solvent control, Fluka) were prepared in Phosphate Buffered Saline (without Ca++ and Mg++, BioConcept).

20 μl/well of extract dilutions and controls, respectively, were added in duplicate wells. Ethanol was added to a final concentration of 0.2% as the solvent control. Cells were incubated for one hour at 37° C. in a 5% $CO_2$ incubator.

Lipopolysaccharide stock was prepared (Sigma, LPS from *E. coli* 055:65, 10 mg/ml in ultrapure water). Shortly before use, the stock solution was sonicated for 2 minutes. LPS was added to 10 g/ml final concentration, and incubated at 37° C. and 5% $CO_2$ for 24 hours.

LPS was added to all sample wells except two wells. These wells were the unstimulated control.

After 24 hours, THP-1 cell culture supernatants were collected for cytokine analysis. The samples in the wells were mixed. The plate was centrifuged to pellet the cells. Cell-free supernatants (140 μl per well) were removed and transferred to a new round-bottom 96 well plate. Plates were sealed, and the supernatants were stored at −80° C. until measurement.

Figure 2:
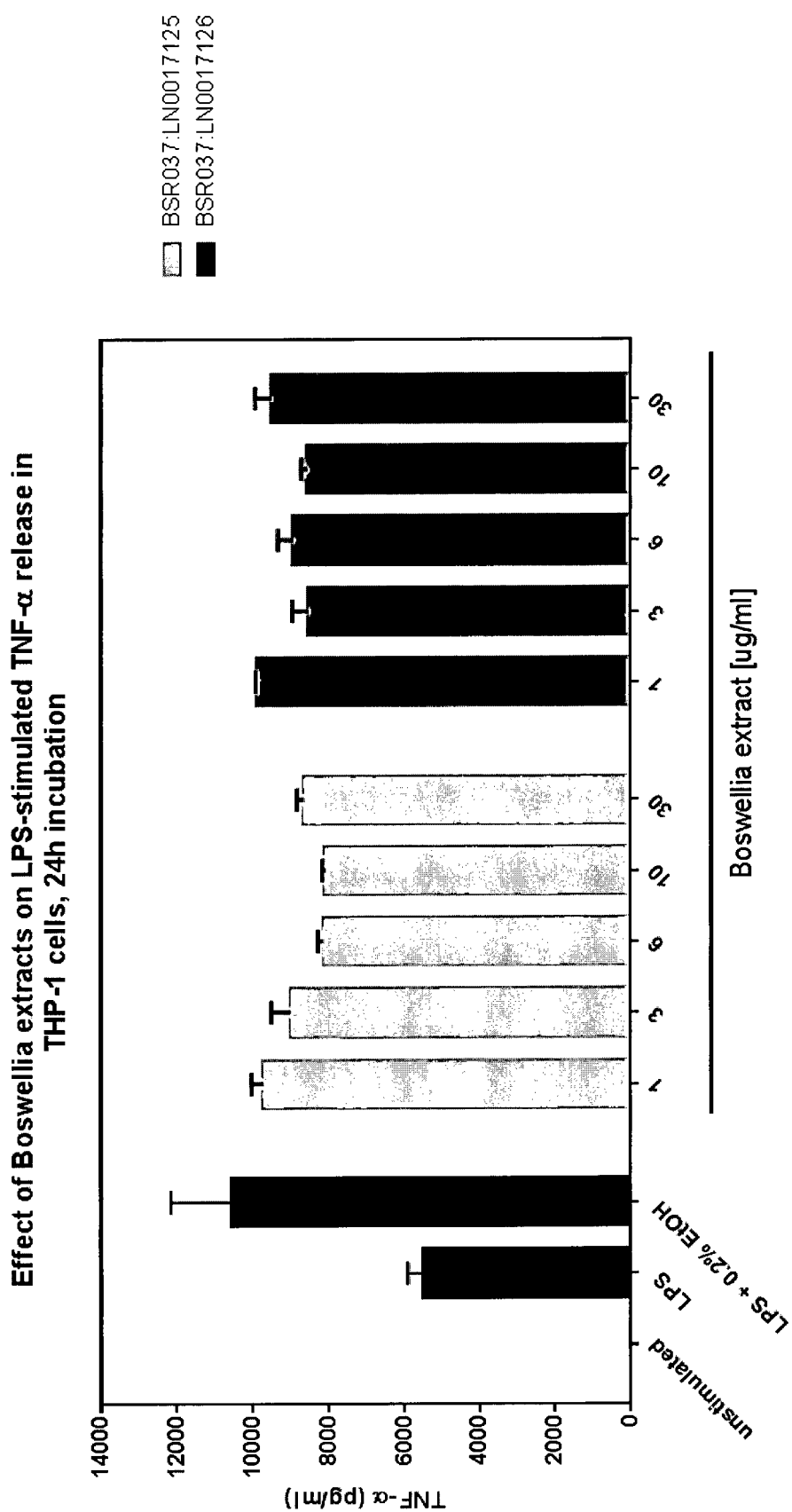
FIG. 2: Effect of *Boswellia* extracts on LPS-stimulated TNF-α release in THP-1 cells
Figure 3:
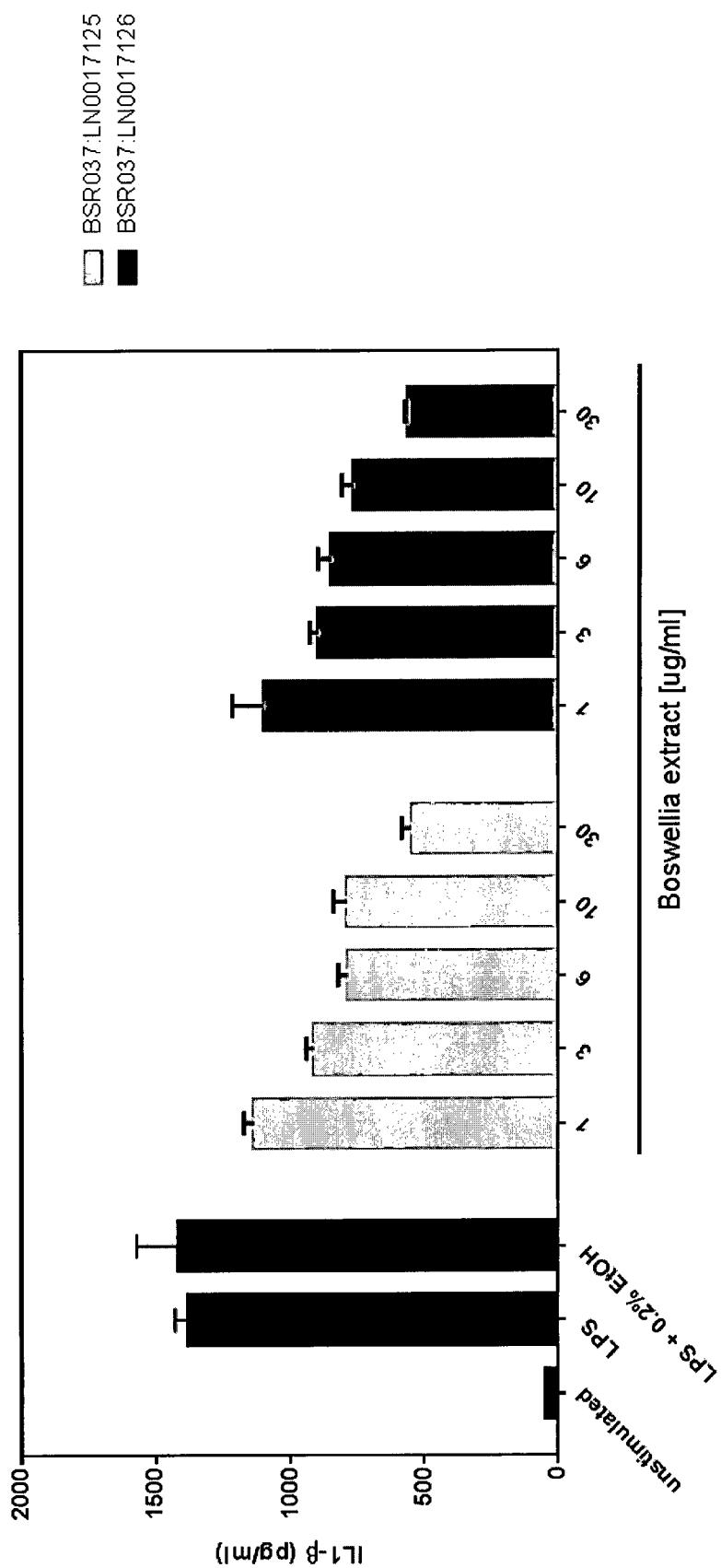
FIG. 3: Effect of *Boswellia* extracts on LPS-stimulated IL1-β release in THP-1 cells
Figure 4:
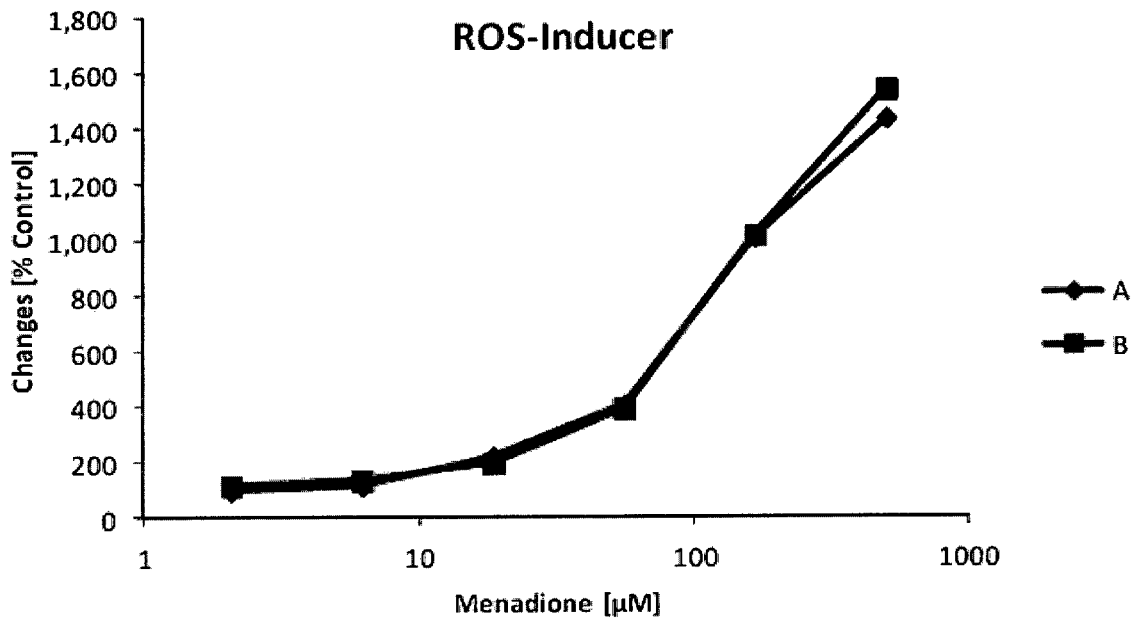
FIG. 4: ROS induction in HepG2 cells
HepG2 cells were exposed to *Boswellia* extracts and controls for two hours and ROS levels were determined. A. Positive control Menadione. B. Negative control ethanol. C. *Boswellia serrata* extract according to Example 12. D. *Boswellia serrata* extract according to Example 15.
Figure 4:
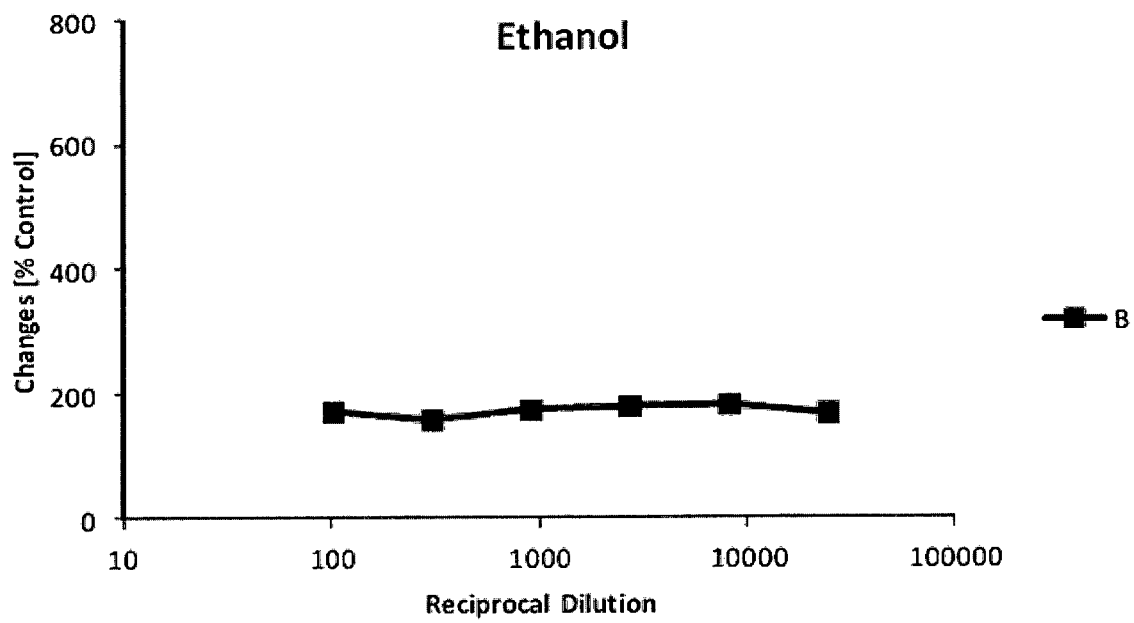
Figure 4:
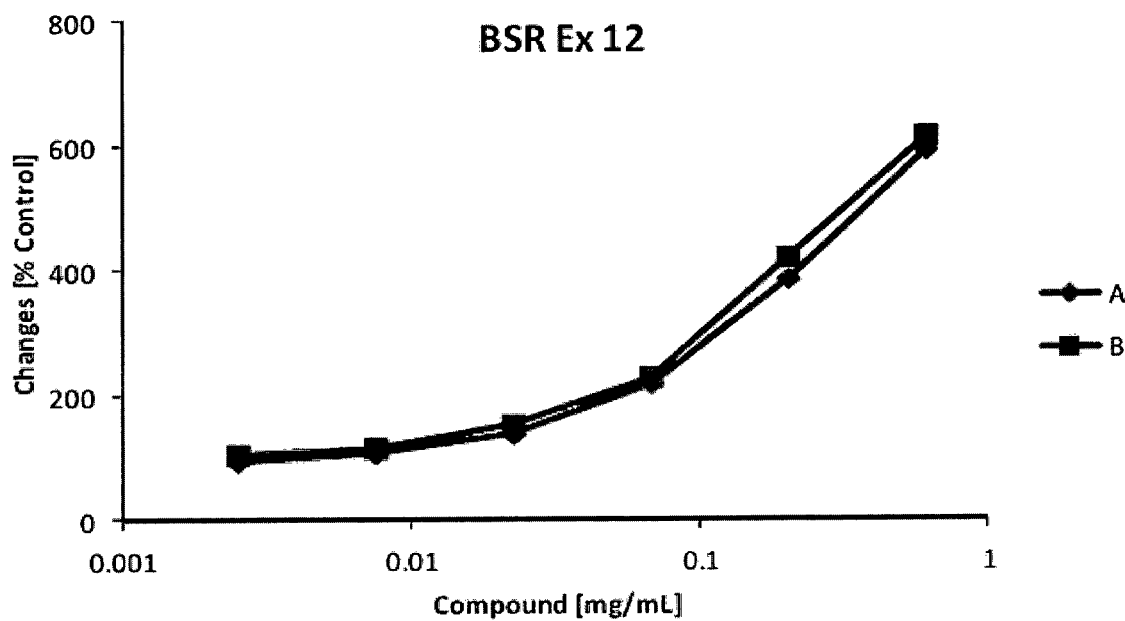
Figure 4:
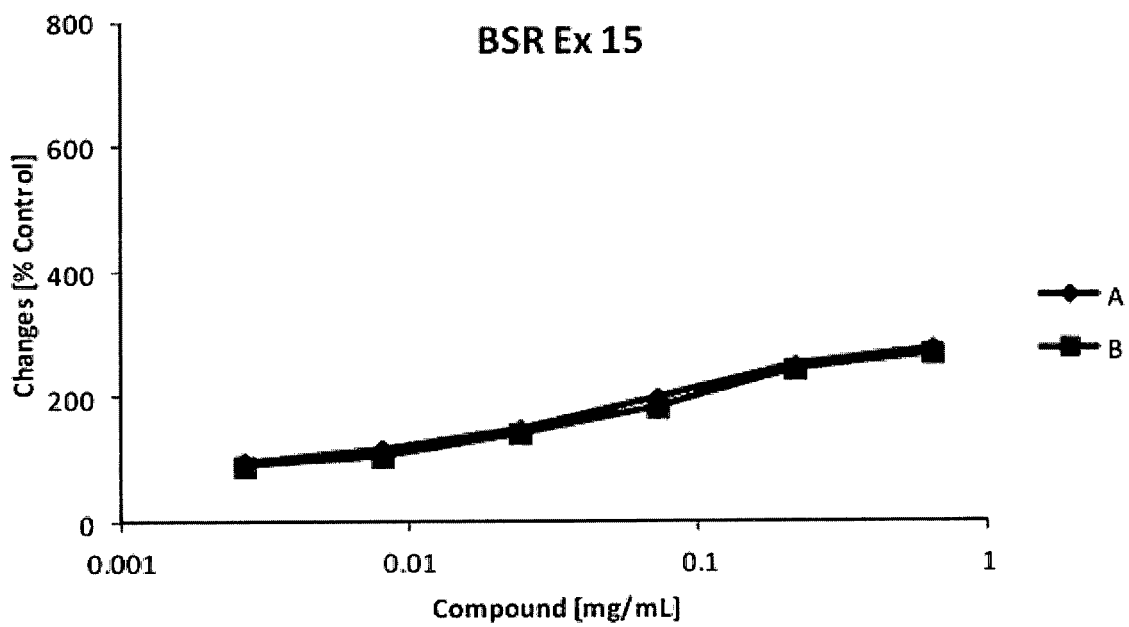
Figure 5:
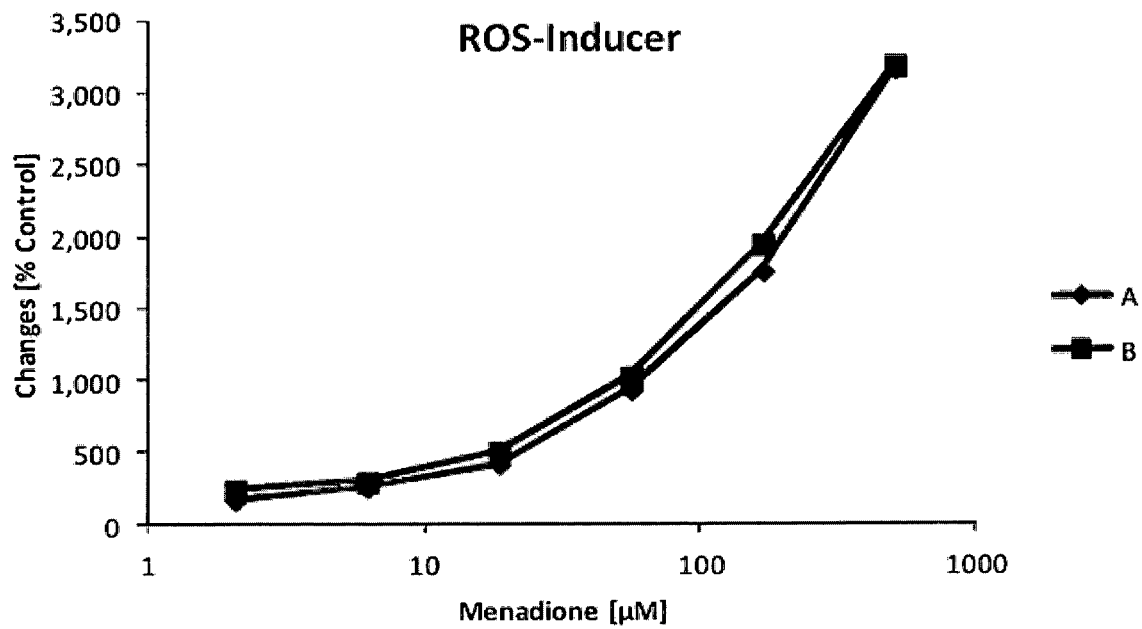
FIG. 5: ROS induction in HepG2 cells
HepG2 cells were exposed to *Boswellia* extracts and controls for four hours and ROS levels were determined. A. Positive control Menadione. B. Negative control ethanol. C. *Boswellia serrata* extract according to Example 12. D. *Boswellia serrata* extract according to Example 15.
Figure 5:
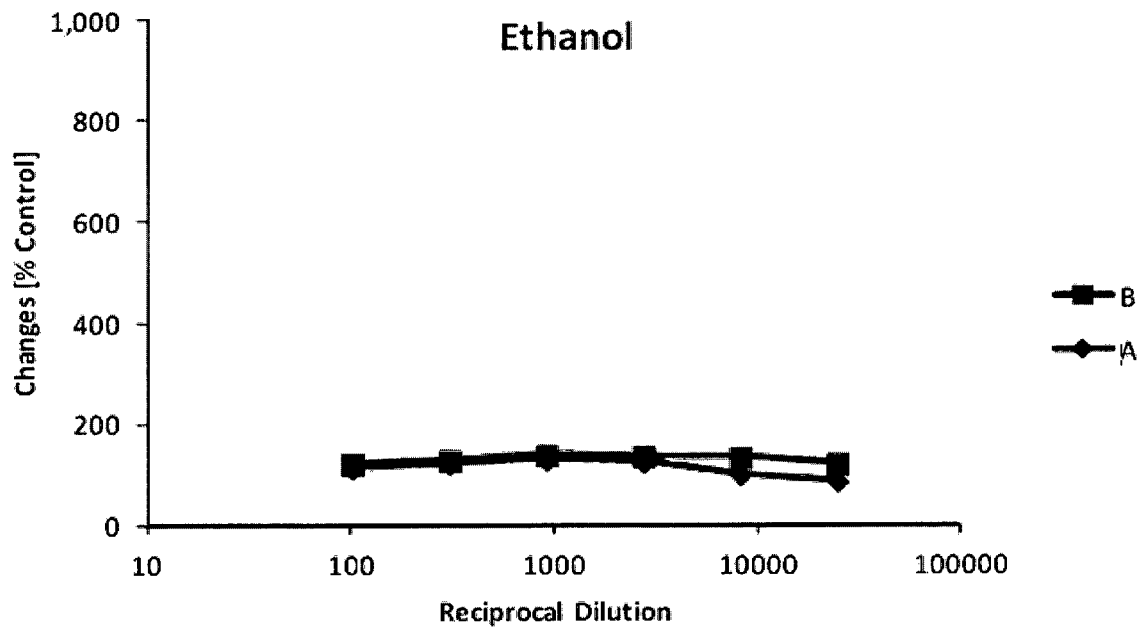
Figure 5:
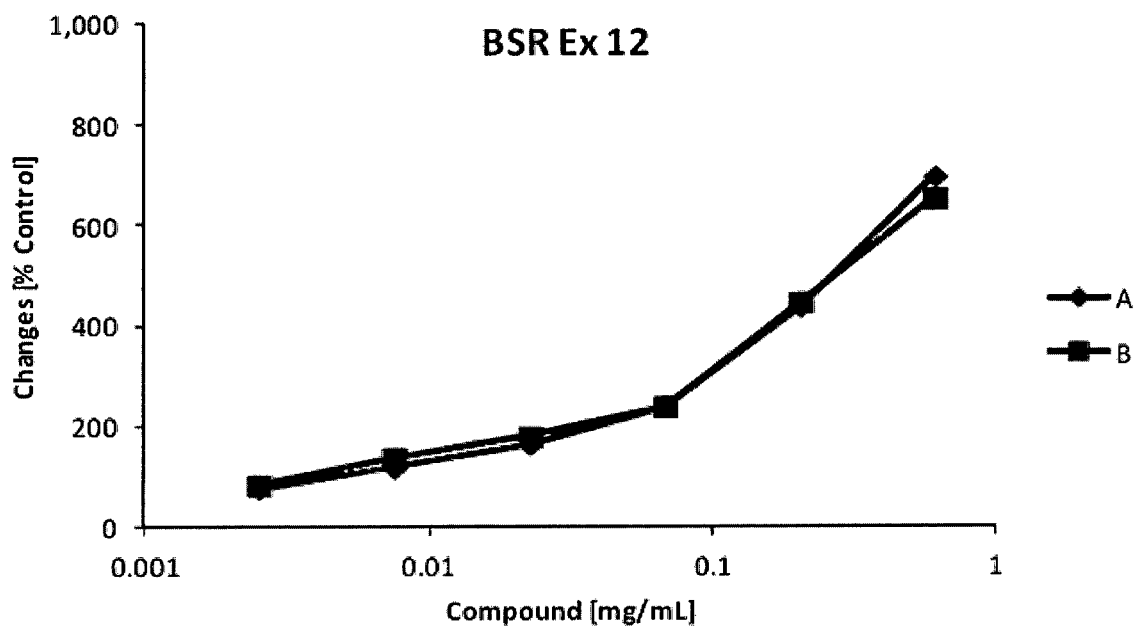
Figure 5:
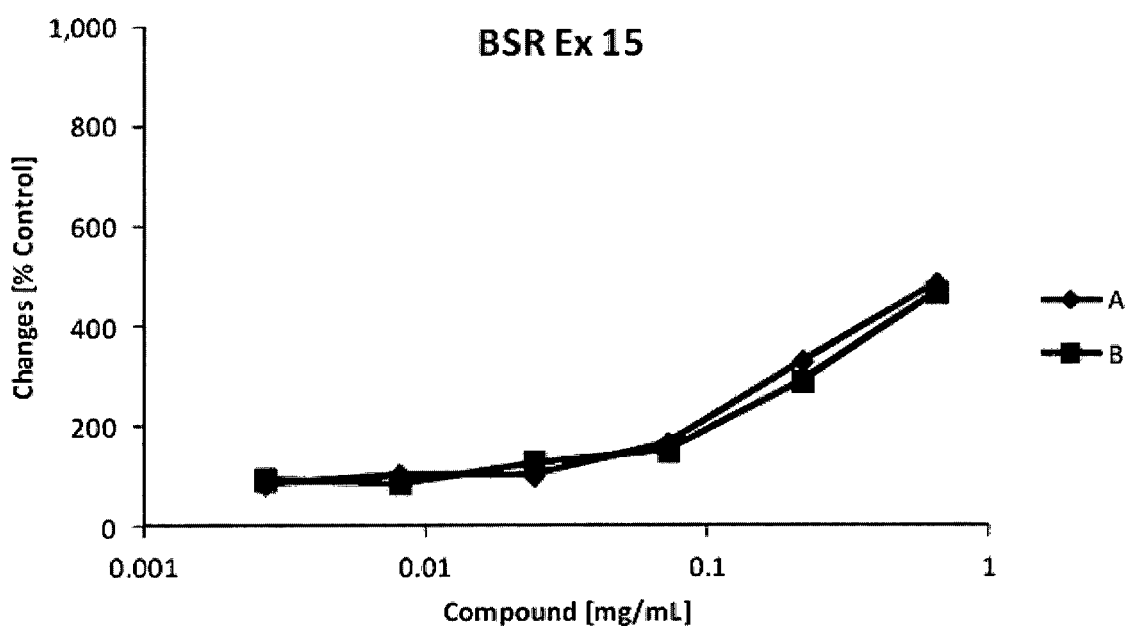

Cytokines were measured in the THP-1 supernatants by DuoSet ELISA from R&D Systems. The levels of IL6 (FIG. 1), TNF-α (FIG. 2) and IL1-β (FIG. 3) were determined.

As a result, *Boswellia* extracts BSR037: LN00125 (Example 12) and BSR037: LN00126 (Example 15) showed anti-inflammatory cytokine patterns as indicated by a dose-dependent reduction of IL6, IL1-β and TNF-α. In comparison to BSR037: LN00126 (Example 15), the extract BSR037: LN00125 (Example 12) showed a more pronounced anti-inflammatory pattern, especially in regard of the reduction of IL1-β and TNF-α cytokine levels.

Example 17 (Determination of Reactive Oxygen Species (ROS) in HepG2 Indicator Cells)

The potential of *Boswellia* extract BSR037: LN00125 (Example 12) and *Boswellia* extract BSR037: LN00126 (Example 15) of inducing reactive oxygen species (ROS) was tested. The effects were compared with ROS generation upon exposure to positive control Menadione as well as two solvent ethanol. To this end, HepG2 cells were incubated in presence of different concentrations of the respective *Boswellia* extract for two hours. ROS levels were determined by using the ROS-Glo system (Promega).

HepG2 cells were seeded in 296-well flat-bottom black microtiter plates at a density of 10000 cells per well, 100 μl per well, and allowed to attach to the plate for 24 hours.

Test item dilutions were prepared in separate plates. The maximum concentration was a 1:100 dilution in media (final solvent concentration: 1% ethanol) followed by a 1:3 serial dilution in media containing 1% ethanol. Positive control compound Menadione was used at a maximum concentration of 500 μM followed by a 1:2 serial dilution. Cells exposed to media containing 1% ethanol served as untreated control.

After overnight adherence, media was completely removed from cells by vacuum aspiration and 80 μl of compound dilution, positive and negative controls were added to the cells. Test items were tested in two replicates per concentration (A and B). In independent experiments, ROS levels were measured after two hours of incubation (see FIG. 4A-D) or after four hours of incubation (see FIG. 5A-D), respectively).

As a result, ROS induction was detected for the positive control Menadione as well as for *Boswellia* extracts BSR037: LN00125 (Example 12) and BSR037: LN00126 (Example 15), wherein BSR037: LS00125 (Example 12) showed a higher potency of ROS induction.

The invention claimed is:

1. An extract from a resin of a plant of genus *Boswellia*, wherein the limonene content, the linalool content, and the thujone content are each less than 20 ppm in the extract and the estragol content is less than 100 ppm in the extract, wherein the limonene content, the linalool content, the thujone content, and the estragol content are each calculated based on the dry weight of the extract.

2. The extract according to claim 1, wherein the limonene content and the thujone content are less than 10 ppm, wherein the limonene content and the thujone content are calculated based on the dry weight of the extract.

3. The extract according to claim 1, wherein the plant is selected from the group consisting of: *Boswellia papyrifera, Boswellia serrata, Boswellia sacra,* and *Boswellia carterii*.

4. The extract according to claim 1, wherein the plant is not *Boswellia papyrifera*.

5. The extract according to claim 1, wherein the essential oil content of the extract is reduced in a relative amount with respect to the resin.

6. The extract according to claim 1, wherein at least one protein interacting polyphenol is reduced in amount in comparison to a conventional extract of the resin.

7. The extract according to claim 6, wherein the protein interacting polyphenol content in the extract is less than 0.10% (w/w), and wherein the protein interacting polyphenol content is calculated based on the dry weight of the extract.

8. The extract according to claim 6, wherein the at least one protein interacting polyphenol is a tannin.

9. The extract according to claim 1, wherein the extract comprises a triterpenic acid or a derivative thereof.

10. The extract according to claim 1, wherein the extract comprises a cyclic diterpenoid or a derivative thereof.

11. The extract according to claim 1, wherein the extract comprises a monocyclic diterpenoid or a derivative thereof.

12. The extract according to claim 1, comprising at least one cyclic diterpenoid or derivative thereof in an amount of at least 4% (w/w) and at least one triterpenic acid or derivative is present in an amount of at least 15% (w/w), calculated based on the dry weight of the extract.

13. The extract according to claim 1, comprising at least one cyclic diterpenoid or derivative thereof in an amount of 10 to 25% (w/w) and at least one triterpenic acid or derivative is present in an amount of 20 to 40% (w/w), calculated based on the dry weight of the extract.

14. A composition comprising the extract of claim 1.

15. The composition according to claim 14, wherein the composition is a pharmaceutical composition and comprises at least one additional pharmaceutically acceptable excipient.

16. The composition according to claim 14, further comprising a second active ingredient.

17. The composition according to claim 14, wherein the composition is selected from the group consisting of a food, a beverage and a food supplement.

* * * * *

UNITED STATES PATENT AND TRADEMARK OFFICE
CERTIFICATE OF CORRECTION

| | | |
|---|---|---|
| PATENT NO. | : 11,759,492 B2 | Page 1 of 1 |
| APPLICATION NO. | : 15/521212 | |
| DATED | : September 19, 2023 | |
| INVENTOR(S) | : Kreuter et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1196 days.

Signed and Sealed this
Nineteenth Day of August, 2025

Coke Morgan Stewart
*Acting Director of the United States Patent and Trademark Office*